(12) United States Patent
Hashimoto et al.

(10) Patent No.: US 8,147,988 B2
(45) Date of Patent: Apr. 3, 2012

(54) PLATINUM COMPLEX AND ORGANIC LIGHT-EMITTING ELEMENT USING SAME

(75) Inventors: Masashi Hashimoto, Tokyo (JP); Satoshi Igawa, Fujisawa (JP); Takao Takiguchi, Chofu (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 745 days.

(21) Appl. No.: 12/261,882

(22) Filed: Oct. 30, 2008

(65) Prior Publication Data

US 2009/0115324 A1    May 7, 2009

(30) Foreign Application Priority Data

Nov. 2, 2007 (JP) ................................. 2007-286104

(51) Int. Cl.
*H01L 51/54* (2006.01)
*C09K 11/06* (2006.01)
(52) U.S. Cl. ........ 428/690; 428/917; 313/504; 313/506; 252/301.16; 257/40; 257/E51.044; 546/4; 546/10
(58) Field of Classification Search .................. None
See application file for complete search history.

(56) References Cited

FOREIGN PATENT DOCUMENTS

| | | | |
|---|---|---|---|
| JP | 2001-181617 A | | 7/2001 |
| JP | 2007-099961 A | * | 4/2007 |
| WO | 2006/067074 A1 | | 6/2006 |

OTHER PUBLICATIONS

English language machine translation of JP 2007-099961 A, 2007.*
"Highly Phosphorescent Bis-Cyclometalated Iridium Complexes:Synthesis,Photophysical Characterization,and Use in Organic Light Emitting Diodes" Lamansky,S.;Djurovich,P.; Murphy,D.;Abdel-Razzaq,F.;Lee,H.-E.;Adachi,C.;Burrows,P.E.; Forrest,S.R.;Thompson,M.E. J.Am.Chem.Soc.;2001;123(18);4304-4312.
"Synthesis and Characterization of Phosphorescent Cyclometalated Platinum Complexes" Brooks,J.;Babayan,Y.;Lamansky,S.; Djurovich,P.I.;Tsyba,I.;Bau,R.;Thompson,M.E. Inorg.Chem.; 2002;41(12);3055-3066.
"Organoplatinum(IV) tris-chelate complexes,each having a cyclic metallacarbonate ring:synthesis,characterization and kineticstudies of the formation" Rashidi,M;Shahabadi,N;Nabavizadeh,M.S. DaltonTrans.;2004;619-622.

* cited by examiner

*Primary Examiner* — Jennifer Chriss
*Assistant Examiner* — Michael H Wilson
(74) *Attorney, Agent, or Firm* — Canon USA Inc. IP Division

(57) ABSTRACT

A platinum complex is represented by General Formula (1) below.

(1)

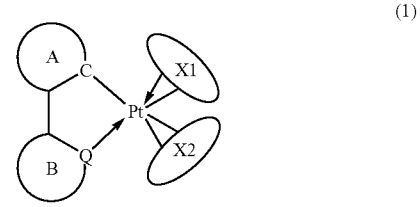

In Formula (1), Pt represents a tetravalent platinum atom. The ring structure A represents a cyclic substituent having a carbon atom that forms a covalent bond with Pt. The ring structure B represents a cyclic substituent having Q that forms a coordination bond with Pt, where Q is a carbon atom, a nitrogen atom, or a phosphorous atom. X1 represents a monovalent-bidentate ligand, and X2 represents a divalent-bidentate ligand.

7 Claims, 6 Drawing Sheets

PLATINUM COMPLEX AND ORGANIC LIGHT-EMITTING ELEMENT USING SAME

BACKGROUND OF THE INVENTION

1. Field of the Invention

The present invention generally relates to a platinum complex and an organic light-emitting element using the same.

2. Description of the Related Art

Light-emitting elements have been actively developed with the object of providing organic LED elements having stable, highly efficient emission. In particular, phosphorescent light-emitting elements using phosphorescence typically have good emission efficiency of the elements themselves. Accordingly, phosphorescent light-emitting materials that are components of phosphorescent light-emitting elements have been intensively developed. A cyclometalated iridium complex of an Ir(C—N)$_3$ type or (C—N)$_2$Iracac type in which a cyclometalated bidentate ligand (C—N ligand, referred to hereinbelow simply as C—N) is coordinated to a metal atom has been disclosed in "Highly Phosphorescent Bis-Cyclometalated Iridium Complexes: Synthesis, Photophysical Characterization, and Use in Organic Light Emitting Diodes", Lamansky, S.; Djurovich, P.; Murphy, D.; Abdel-Razzaq, F.; Lee, H.-E.; Adachi, C.; Burrows, P. E.: Forrest, S. R.; Thompson, M. E. J. Am. Chem. Soc.; 2001; 123 (18); 4304-4312. Also developed have been cyclometalated platinum complexes as disclosed in "Synthesis and Characterization of Phosphorescent Cyclometalated Platinum Complexes" Brooks, J.; Babayan, Y.; Lamansky, S.; Djurovich, P. I.; Tsyba, I.; Bau, R.; Thompson, M. E. Inorg. Chem; 2002; 41 (12); 3055-3066.

However, there remains a need for elements with a light output of even higher luminance and a higher conversion efficiency. Furthermore, in certain instances, the durability of the elements may not be sufficient, with insufficient durability often being associated with degradation in long-term use and resistance to oxygen-containing atmosphere and moisture. In addition, blue, green, and red light emission with good color purity may be necessary when applications to full-color displays and the like are considered. Thus, there remains a need for improved durability and color purity.

Tetravalent platinum complex compounds composed of three bidentates having bipyridine or phenanthroline as a ligand have been disclosed in "Organoplatinum (IV) tris-chelate complexes, each having a cyclic metallacarbonate ring: synthesis, characterization and kinetics studies of the formation" Rashidi, M.; Shahabadi, N.; Nabavizadeh, M. S. Dalton Trans.; 204; 619-622.

Japanese Patent Laid-Open No. 2001-181617 and International Publication No. WO 2006/067074 disclose the application of particular platinum complexes to organic light-emitting elements. More specifically, Japanese Patent Laid-Open No. 2001-181617 discloses the application of a divalent platinum complex material to an organic light-emitting element. International Publication No. WO 2006/067074 discloses the application of a divalent platinum complex material having a carbene ligand to an organic light-emitting element.

SUMMARY OF THE INVENTION

In one embodiment, a platinum complex in accordance with the present invention is represented by a General Formula (1) below

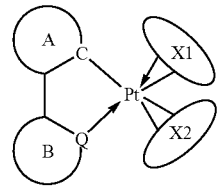

(1)

wherein in the General Formula (1) Pt represents a tetravalent platinum atom; the ring structure A represents a cyclic substituent having a carbon atom that forms a covalent bond with Pt, and may also optionally contain at least one of a halogen atom, a nitro group, a substituted or unsubstituted aryl group, a substituted or unsubstituted heteroaryl group, a disubstituted amino group, and a linear or branched alkyl group having 1 to 20 carbon atoms; the ring structure B represents a cyclic substituent having Q that forms a coordination bond with Pt, wherein Q is a carbon atom, a nitrogen atom, or a phosphorous atom, and the ring structure B may also optionally contain at least one of a halogen atom, a nitro group, a substituted or unsubstituted aryl group, a substituted or unsubstituted heteroaryl group, a disubstituted amino group, and a linear or branched alkyl group having 1 to 20 carbon atoms; wherein, optionally, a new ring structure may be formed by binding a substituent of the ring structure A to a substituent of the ring structure B; X1 represents a monovalent-bidentate ligand; and X2 represents a divalent-bidentate ligand.

Further features of the present invention will become apparent from the following description of exemplary embodiments (with reference to the attached drawings).

DESCRIPTION OF THE EMBODIMENTS

Figure 1:
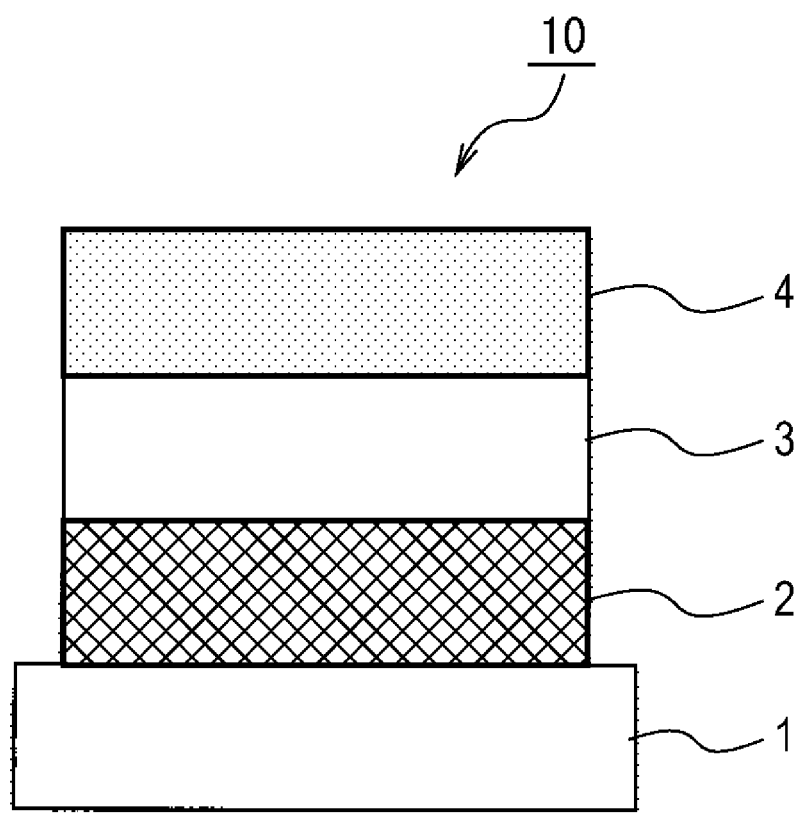
FIG. 1 is a cross-sectional view illustrating a first embodiment of an organic light-emitting element in accordance with the present invention.

The platinum complex in accordance with the present invention will be described below. In one embodiment, the platinum complex in accordance with the present invention is represented by the General Formula (1) below.

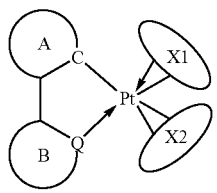
(1)

In Formula (1), Pt represents a tetravalent platinum atom.

Also in Formula (1), the ring structure A represents a cyclic substituent having a carbon atom (C) that forms a covalent bond with Pt. In one version, the ring structure A is an aromatic cyclic substituent.

Examples of cyclic substituents represented by the ring structure A may include, but are not limited to, a phenyl group, a naphthyl group, an anthonyl group, a fluorenyl group, a pyrenyl group, a phenanthrenyl group, a chrysenyl group, a fluoranthenyl group, a triphenylenyl group, a cyclopentenyl group, a cyclohexenyl group, a cyclohexadienyl group, a norbornenyl group, a pyridyl group, a pyrazinyl group, a pyrimidyl group, a pyridazinyl group, a quinolinyl group, an isoquinolinyl group, a phenanthridinyl group, an acridinyl group, a naphthylidinyl group, a quinoxalinyl group, a quinazolinyl group, a cinnolinyl group, a phthaladinyl group, a phenanthrolyl group, a phenadinyl group, a thiazolyl group, a thienyl group, a furanyl group, a pyrrolyl group, an imidazolyl group, a thiazolyl group, a benzothienyl group, a benzofuranyl group, an indolyl group, a dibenzothienyl group, a dibenzofuranyl group, and a carbazolyl group.

For example, in one version, the cyclic substituent may be a phenyl group, a naphthyl group, a fluorenyl group, a phenanthrenyl group, a triphenylenyl group, a cyclopentenyl group, a pyridyl group, a pyrazinyl group, a pyrimidyl group, a pyridazinyl group, a quinolinyl group, an isoquinolinyl group, a quinoxalinyl group, a thienyl group, a benzothienyl group, a dibenzofuranyl group, or a carbazolyl group. In yet another version, the cyclic substituent may be a phenyl group, a fluorenyl group, a pyridyl group, a thienyl group, a dibenzofuranyl group, or a carbazolyl group. As another example, the cyclic substituent may be a phenyl group, a fluorenyl group, a thienyl group, or a carbazolyl group.

The ring structure A may also optionally have, i.e. be substituted by, at least one of a halogen atom, a nitro group, a substituted or unsubstituted aryl group, a substituted or unsubstituted heteroaryl group, a disubstituted amino group, and a linear or branched alkyl group having 1 to 20 carbon atoms. For example, the ring structure A may have any one of these substituents, or may have two or more of any of these substituents, or may have two or more kinds of these substituents.

Examples of halogen atom substituents can include, but are not limited to, a fluorine atom, a chlorine atom, and a bromine atom. For example, in an embodiment where the element is fabricated by a vacuum vapor deposition method, a suitable halogen atom may be a fluorine atom.

Examples of aryl group substituents can include, but are not limited to, a phenyl group, a naphthyl group, an anthonyl group, a fluorenyl group, a pyrenyl group, a phenanthrenyl group, a chrysenyl group, a fluoranthenyl group, and a triphenylenyl group. For example, in one version, the aryl group may be a phenyl group, a naphthyl group, an anthonyl group, a fluorenyl group, a pyrenyl group, a phenanthrenyl group, a chrysenyl group, a fluoranthenyl group, or a triphenylenyl group. In another version, the aryl group may be a phenyl group, a fluorenyl group, a phenanthrenyl group, or a triphenylenyl group. In yet another version, the aryl group may be a phenyl group.

The substituent represented by the aryl group may even be substituted with a further substituent. Specific examples of such substituents can include, but are not limited to, alkyl groups such as a methyl group, a tert-butyl group, and a trifluoromethyl group; halogen atoms such as a fluorine atom and a chlorine atom; and substituted amino groups such as a diphenylamino group and a di-tert-butyl amino group.

Examples of heteroaryl group substituents can include, but are not limited to, a pyridyl group, a pyrazinyl group, a pyrimidyl group, a pyridazinyl group, a triazinyl group, a quinolinyl group, an isoquinolinyl group, phenanthridinyl group, an acridinyl group, a naphthylidinyl group, a quinoxalinyl group, a quinazolinyl group, a cinnolinyl group, a phthaladinyl group, a carbazolyl group, a phenanthrolyl group, a thiazolyl group, an isothiazolyl group, an imidazolyl group, a pyrazolyl group, an oxazolyl group, an isooxazolyl group, a benzothiazolyl group, a benzoisothiazolyl group, a benzoimidazolyl group, a benzopyrazolyl group, a benzoxazolyl group, and a benzoisooxazolyl group. For example, in one version, the heteroaryl group may be a pyridyl group, a pyrazinyl group, a pyrimidyl group, a triazinyl group, a quinolinyl group, an isoquinolinyl group, a thiazolyl group, an imidazolyl group, a pyrazolyl group, or an oxazolyl group. In yet another version, the heteroaryl group may be a pyridyl group or an imidazolyl group.

The substituent represented by the heteroaryl group may even be substituted with a further substituent. Specific examples of such substituents can include, but are not limited to, substituents identical to the above-described substituents that may be contained in the aryl group.

Examples of disubstituted amino group substituents may include, but are not limited to, a dimethylamino group, a diphenylamino group and a ditolylamino group, which may be capable of providing suitable electrical conductivity levels. In one version, the disubstituted amino group substituent may be a diphenylamino group.

Examples of alkyl group substituents may include, but are not limited to, a methyl group, an ethyl group, an n-propyl group, an isopropyl group, an n-butyl group, a tert-butyl group, an octyl group, and a cyclohexyl group. In the case of the alkyl group having two or more carbon atoms, one, or two or more non-adjacent methylene groups (—CH$_2$—) in the alkyl group may be substituted with —O—, —S—, —CO—. Examples of the alkyl groups in which the methylene group is substituted with —O—, —S—, —CO— include a methoxy group, an ethoxy group, and a methylsulfanyl group. Some or all of the hydrogen atoms in the alkyl group may also be substituted with fluorine atoms. A trifluoromethyl group is an example of an alkyl group substituted with a fluorine atom.

In one version, the alkyl groups (including those in which a methylene group is substituted with —O— and the like and those in which some or all of the hydrogen atoms are substituted with fluorine atoms) can include, but are not limited to, a methyl group, an ethyl group, a tert-butyl group, a trifluoromethyl group, a methoxy group, and a methylsulfanyl group. In yet another version, the alkyl group may be a methyl group, a tert-butyl group, a trifluoromethyl group, or a methoxy group.

In Formula (1), the ring structure B represents a cyclic substituent having Q that forms a coordination bond with Pt. Examples of Q can include a carbon atom, a nitrogen atom, or a phosphorus atom. For example, in one version, Q may be a nitrogen atom.

Examples of cyclic substituents represented by the ring structure B can include, but are not limited to, a pyridyl group, a pyrazinyl group, a pyrimidyl group, a pyridazinyl group, a triazinyl group, a quinolinyl group, an isoquinolinyl group, a phenanthridinyl group, an acridinyl group, a naphthylidinyl group, a quinoxalinyl group, a quinazolinyl group, a cinnolinyl group, a phthaladinyl group, a phenanthrolyl group, a thiazolyl group, an isothiazolyl group, an imidazolyl group, a pyrazolyl group, an oxazolyl group, an isooxazolyl group, a benzothiazolyl group, a benzoisothiazolyl group, a benzoimidazolyl group, a benzopyrazolyl group, a benzoxazolyl group, a benzoisooxazolyl group, and an oxazolyl group. In one version, the cyclic substituent may be a pyridyl group, a pyrazinyl group, a pyrimidyl group, a triazinyl group, a quinolinyl group, an isoquinolinyl group, a quinoxalinyl group, a phenanthrolyl group, a thiazolyl group, an isothiazolyl group, an imidazolyl group, a pyrazolyl group, an oxazolyl group, or an isooxazolyl group. In another version, the cyclic substituent may be a pyridyl group, a thiazolyl group, an isothiazolyl group, an imidazolyl group, or a pyrazolyl group.

The ring structure B may also optionally contain, i.e. be substituted by, at least one of a halogen atom, a nitro group, a substituted or unsubstituted aryl group, a substituted or unsubstituted heteroaryl group, a disubstituted amino group, and a linear or branched alkyl group having 1 to 20 carbon atoms. Specific examples of the halogen atom, aryl group, heteroaryl group, disubstituted amino group, and alkyl group can include, but are not limited to, those identical to the above-described specific examples of the halogen atom, aryl group, heteroaryl group, disubstituted amino group, and alkyl group that may be present in the ring structure A. Furthermore, specific examples of substituents that may be further present in the aryl group and the heteroaryl group can include, but are not limited to, those identical to the above-described specific examples of substituents that may be further present in an aryl group present in the ring structure A. The ring structure B may have any one of these substituents, or may have two or more of any of these substituents, or may have two or more kinds of these substituents.

In yet another version, a new ring structure may optionally be formed by coupling (i.e. binding) a substituent of the ring structure A to a substituent of the ring structure B. Partial structures that include a ligand containing a new ring structure formed by coupling a substituent of the ring structure A to a substituent of the ring structure B are shown below. However, these are intended merely as representative examples and the present invention is not limited thereto.

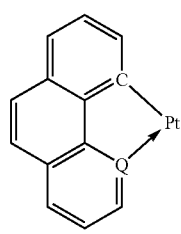

A001

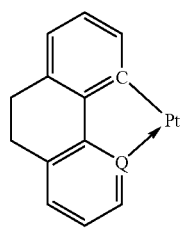

A002

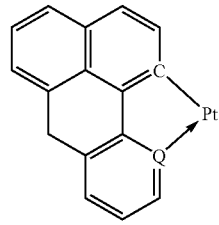

A003

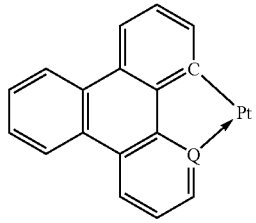

A004

In Formula (1) above, X1 represents a monovalent-bidentate ligand, and X2 represents a divalent-bidentate ligand. An atom forming a coordination bond with the platinum atom is not particularly limited, but may be, for example a nitrogen atom, a phosphorus atom, a carbon atom, an oxygen atom, or a sulfur atom. Further, an atom forming a covalent bond with the platinum atom is not particularly limited, but may be, for example, a carbon atom, a nitrogen atom, an oxygen atom, a sulfur atom, or a phosphorus atom.

Furthermore, in one embodiment X1 may be a ligand represented by B000 of the following formula. The ligand B000 represented by the following formula is shown in a state of being coupled to a platinum atom.

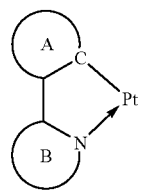

Specific examples of ligands represented by X1 are shown below. However, these are intended merely as representative examples, and the present invention is not limited thereto. The ligands presented below are shown in a state of being coupled to the platinum atom.

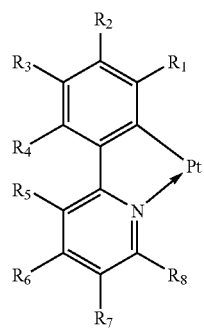

B001

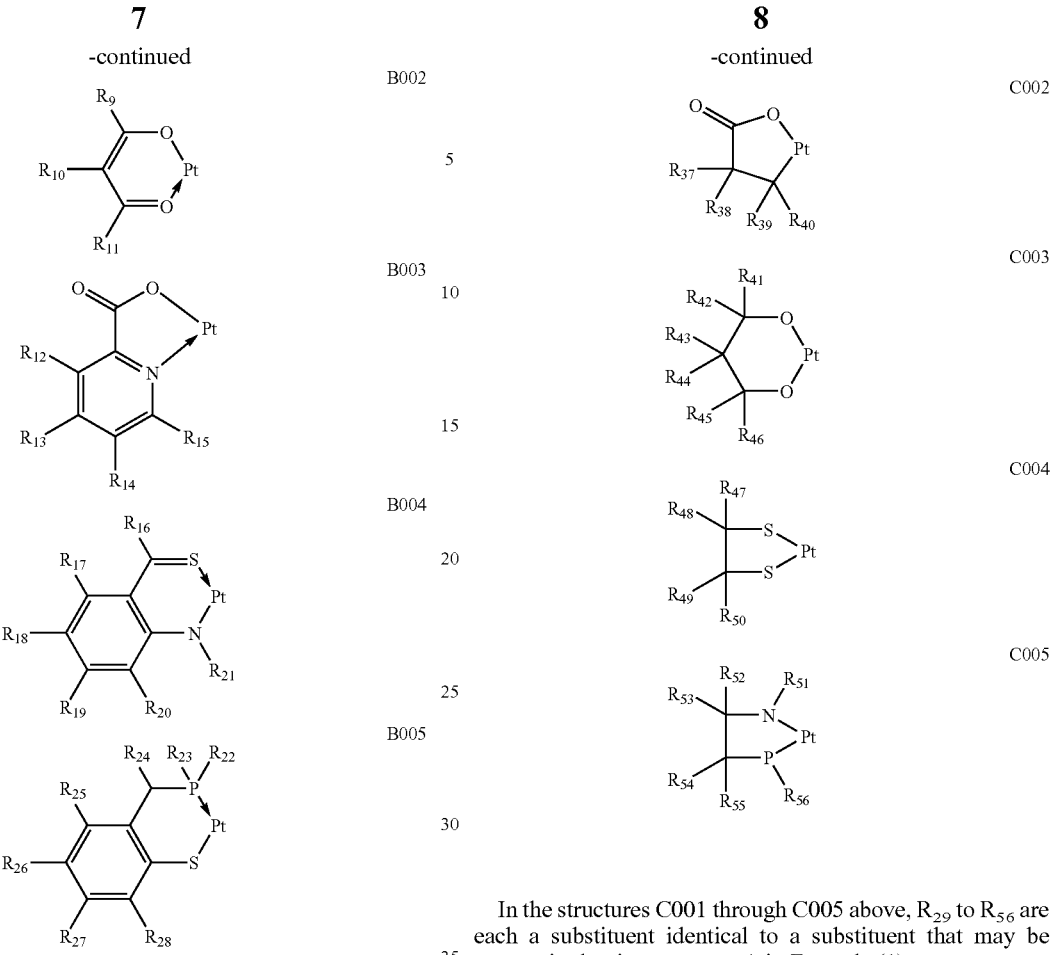

In the structures B001 through B005 above, $R_1$ to $R_{28}$ are each a substituent identical to a substituent that may be present in the ring structure A in Formula (1).

In Formula (1), X2 represents a divalent-bidentate ligand. An atom forming a coordination bond with the platinum atom is not particularly limited, but may be, for example, a carbon atom, a nitrogen atom, an oxygen atom, a sulfur atom, or a phosphorus atom.

Furthermore, in one version, X2 may be a bidentate ligand having a carbon atom and an oxygen atom that form covalent bonds with a platinum atom.

Specific examples of ligands represented by X2 are shown below. However, these are inteneded merely as representative examples, and the present invention is not limited thereto. The ligands presented below are shown in a state of being coupled to the platinum atom.

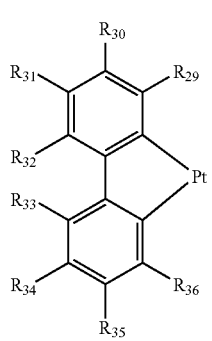

In the structures C001 through C005 above, $R_{29}$ to $R_{56}$ are each a substituent identical to a substituent that may be present in the ring structure A in Formula (1).

In one embodiment, the platinum complex in accordance with the present invention may be represented by the following General Formula (2)

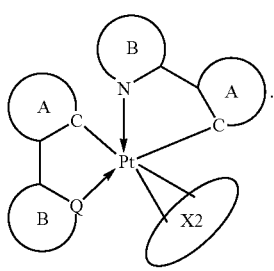

(2)

Specific examples of the ring structure A and B, bidentate ligand X2, and Q in Formula (2) are identical to the specific examples of the ring structure A and B, bidentate ligand X2, and Q in the platinum complex represented by the General Formula (1), as described above.

In one version, the platinum complex in accordance with the present invention can be synthesized, for example, by the following synthesis routine. However, the synthesis routine shown below is merely a representative example and a synthesis method for the platinum complex in accordance with the present invention is not limited thereto.

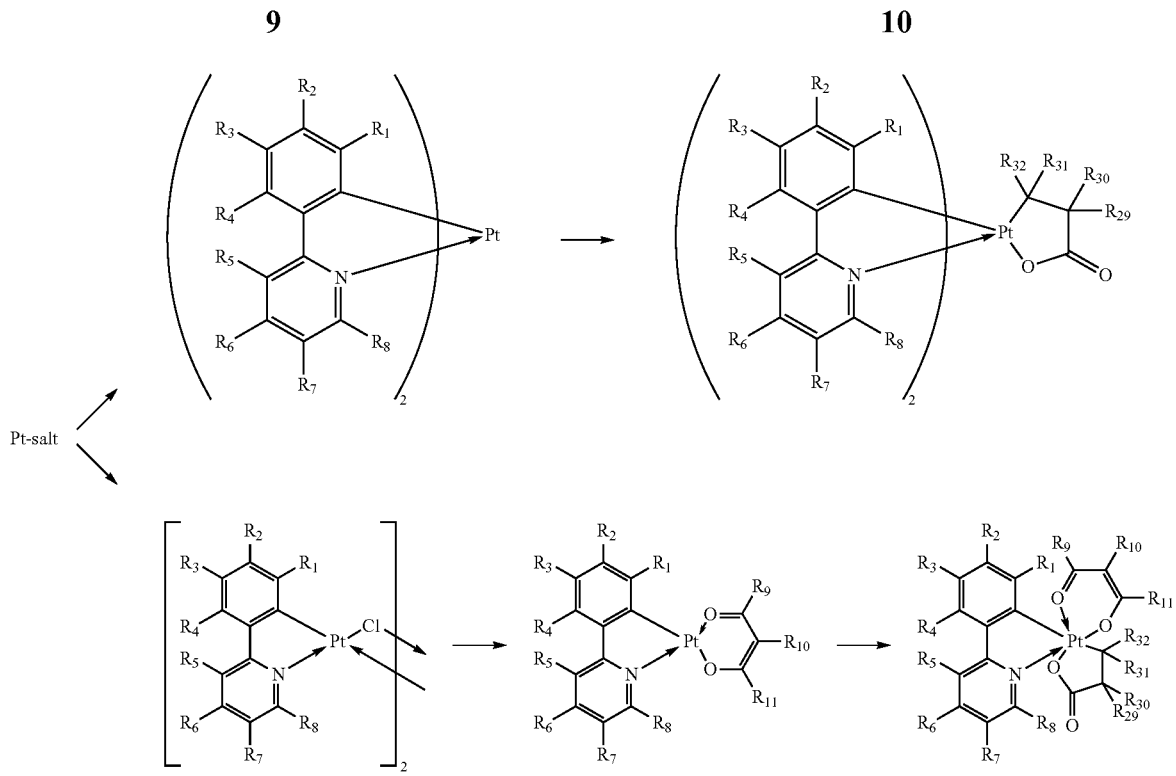

Furthermore, in one version the platinum complex in accordance with the present invention may be used after sufficient purification. Admixed impurities are often a reason for light emission deterioration caused by electric current. However, when polymer compounds are used as constituent materials of the element, impurities present in the polymer compounds may be difficult to remove. Therefore, the impurities may easily become admixed into the element, shortening the service life of the element. By contrast, because the platinum complex in accordance with the present invention is a monomolecular compound, by using a suitable purification method such as a recrystallization method, a column chromatography method, or a sublimation purification method, it may be possible to relatively easily remove the impurities. Therefore, durability of the organic light-emitting element can be improved.

The platinum complex in accordance with the present invention has the following properties.

(i) An organometallic complex having a tetravalent platinum atom as a central metal.

(ii) A neutral (non-ionic) organometallic complex having three bidentate ligands.

(iii) All three ligands are coupled to the central metal via at least one covalent bond.

Furthermore, because the platinum complex in accordance with the present invention is an organometallic complex having a tetravalent platinum atom as a central metal, the complex may demonstrate the following effects.

The coordination of the ligands constituting the complex to the central metal is of a steric octahedral form. The resultant effect may be that light quenching by stacking between identical molecules and variation in the emission color caused by the formation of excimers is inhibited.

By contrast with the platinum complex in accordance with the present invention, in an organometallic complex having a divalent platinum complex as a central atom (referred to hereinbelow as "divalent platinum complex"), the coordination is of a planar tetragonal ligand form. Therefore, because a divalent platinum complex has a planar shape, it is believed that light quenching caused by stacking between identical molecules and formation of excimers can more easily occur. Therefore, this can be the reason for a decrease in emission efficiency and variation of emission color when a divalent platinum complex is used as a light-emitting material.

Furthermore, because the platinum complex in accordance with the present invention is a neutral (non-ionic) organometallic complex, the following effects may be demonstrated.

When an organic light-emitting element is fabricated using a vacuum vapor deposition method, a neutral organometallic complex may often be more advantageous from the standpoint of sublimation ability of the material and also because there is no interaction of ionic properties between the complexes. Furthermore, from the standpoint of heat resistance that may become a problem when vacuum vapor deposition is used, an organometallic complex having multidentate ligands with a higher coordination force may provide improved heat resistance over organometallic complexes having a monodentate ligand.

In the platinum complex in accordance with the present invention, because three ligands are all coupled to the central metal via at least one covalent bond the following effects may also be demonstrated.

Since the platinum atom and each ligand are coupled by at least one covalent bond, the bond force between the platinum atom, which is the central metal, and each of the ligands, is strong. Therefore, heat resistance of the complex itself may be further increased.

Specific structural formulas of the light-emitting element material used in accordance with embodiments of the present invention will be shown below. However, these are merely representative examples and the present invention is not intended to be limited thereto.

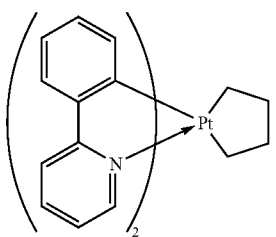 M001
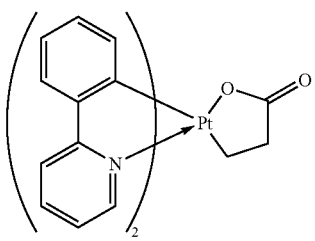 M007
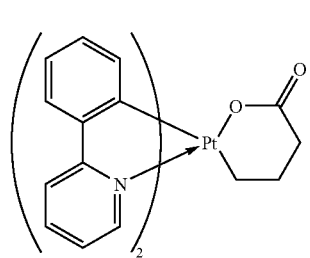 M008
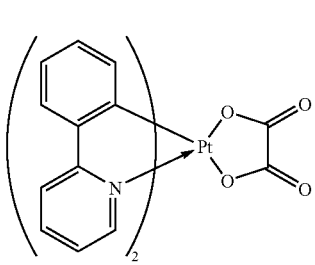 M009
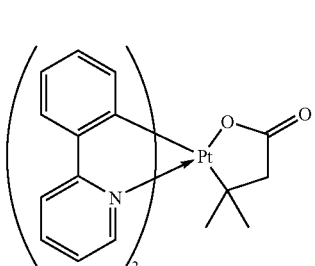 M010
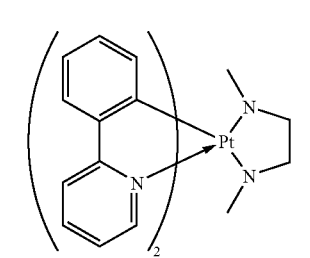 M011
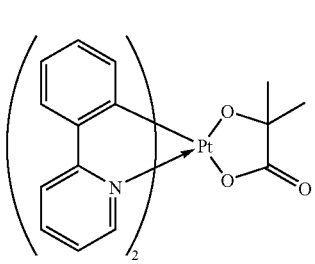 M012

M013 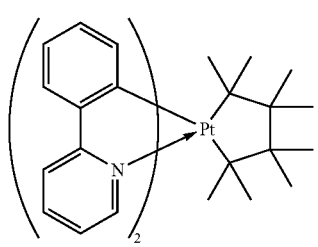
M014 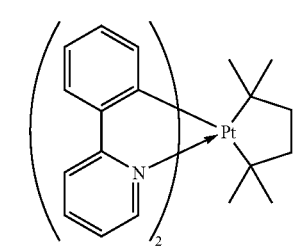
M015 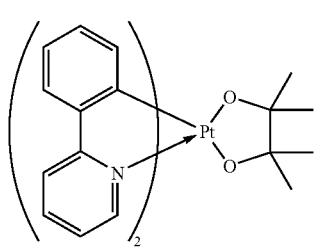
M016 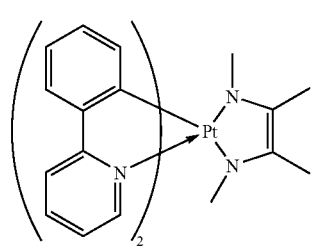
M017 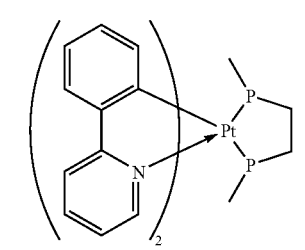
M018 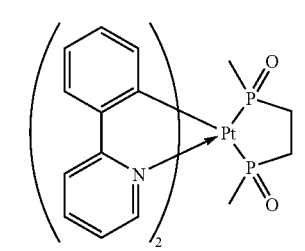
M019 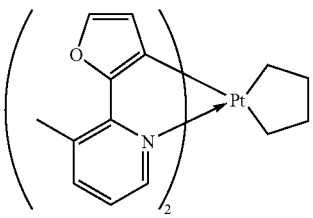
M020 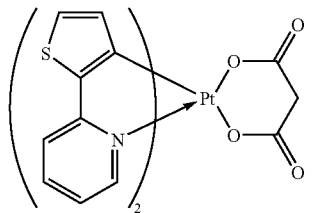
M021 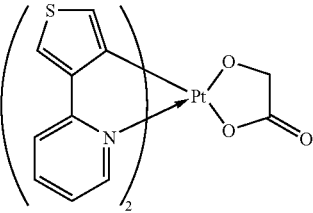
M022 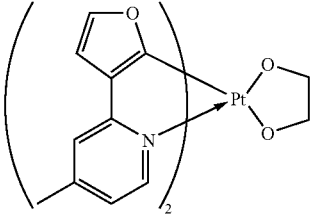
M023 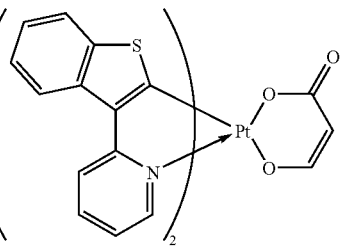
M024 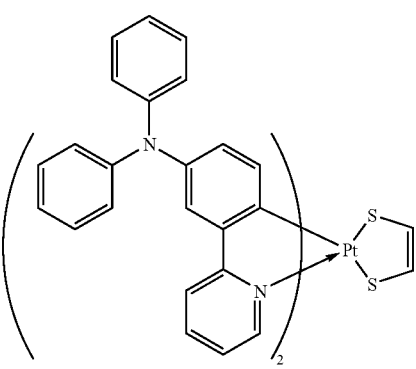

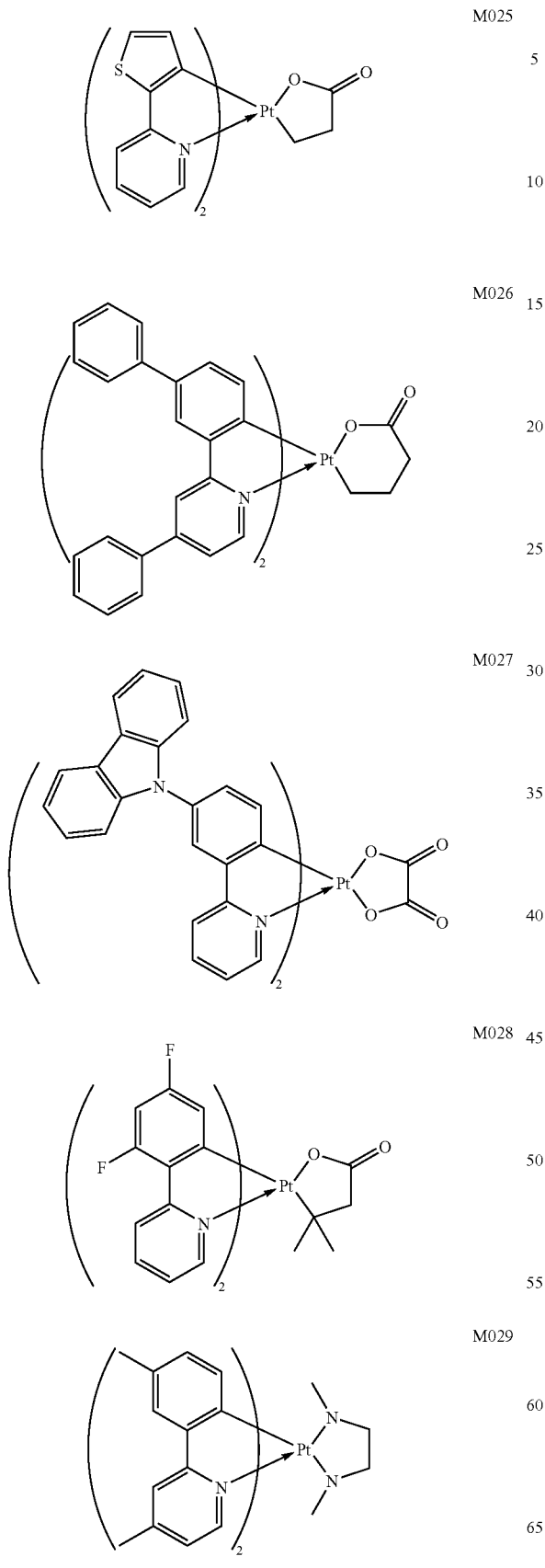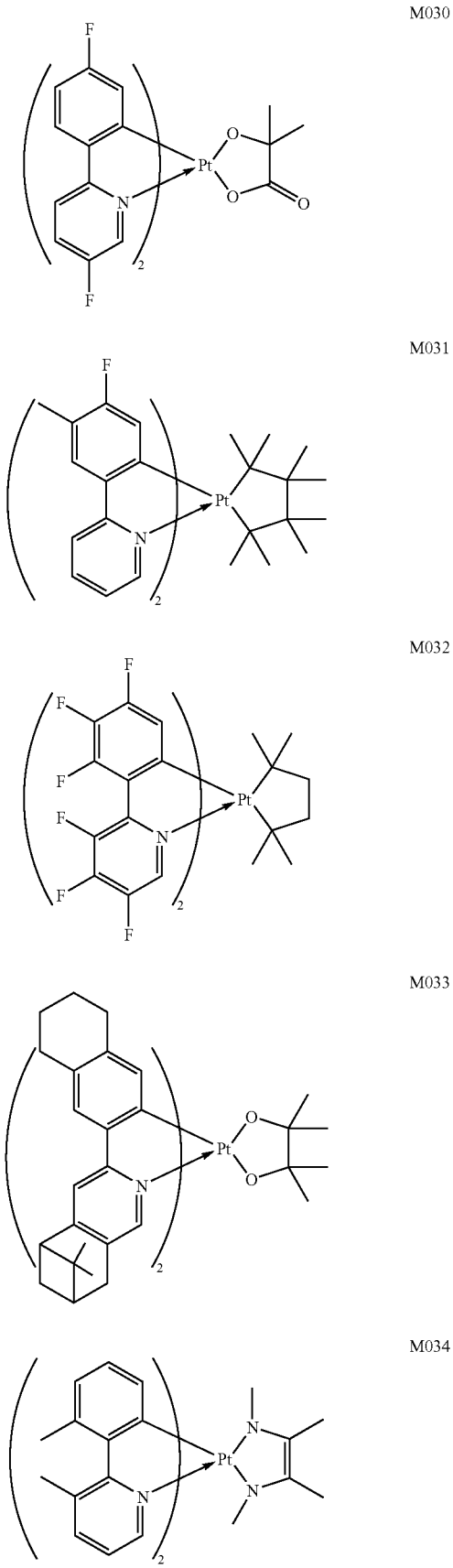

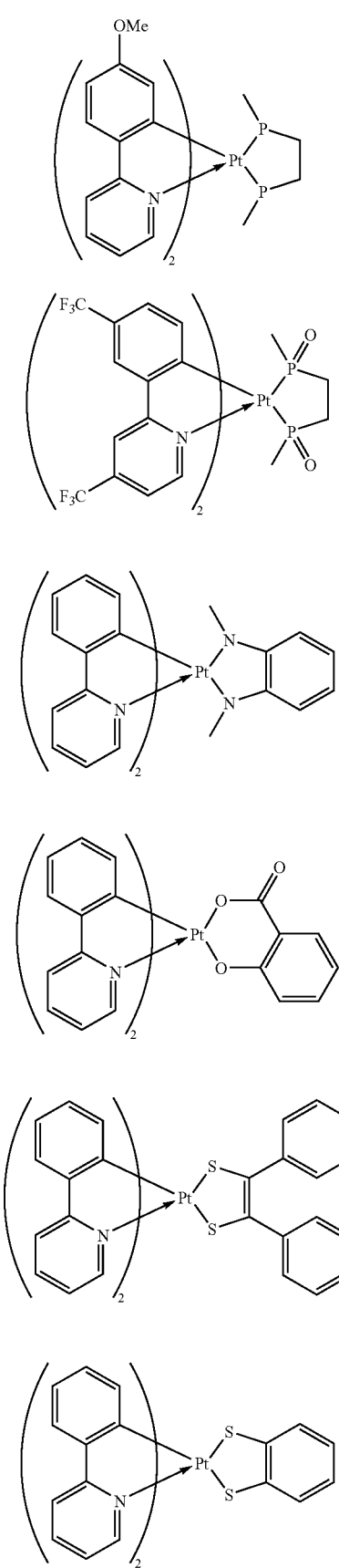

M044
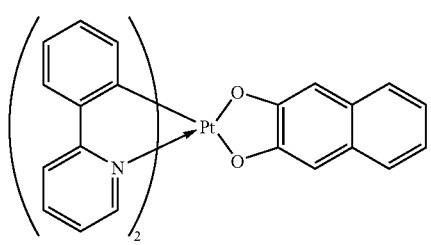
M045
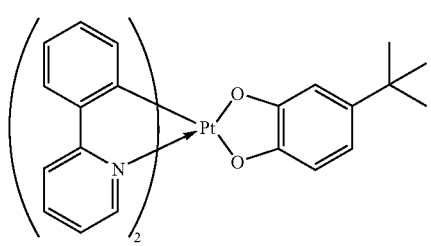
M046
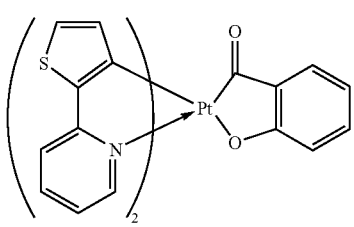
M047
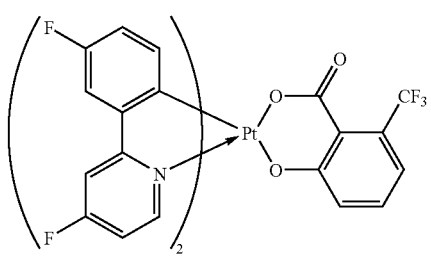
M048
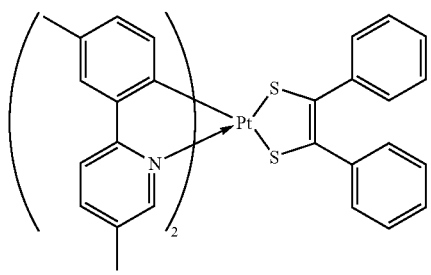
M049
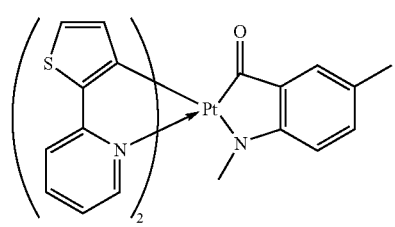
M050
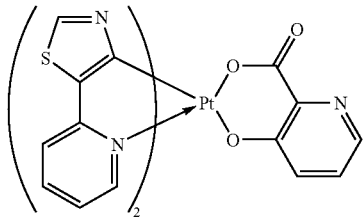
M051
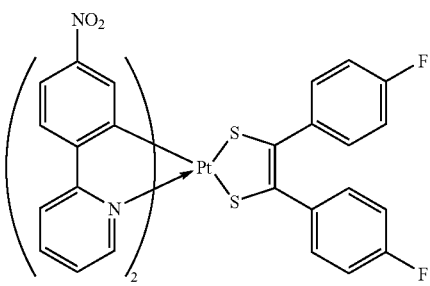
M052
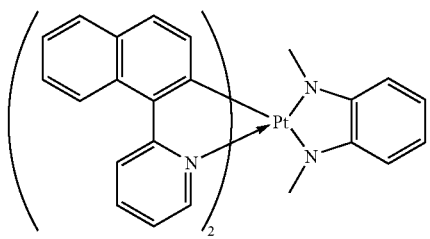
M053
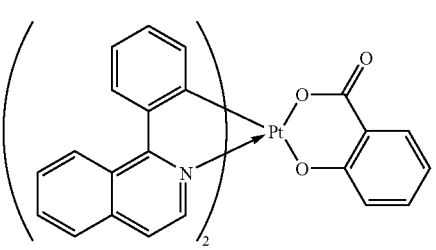
M054
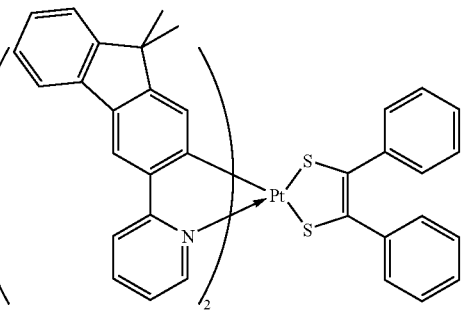
M055
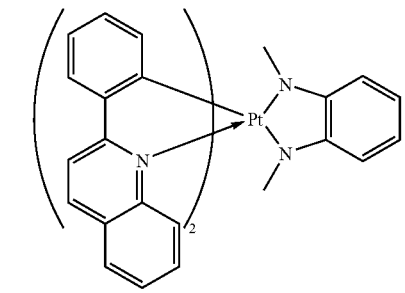

M056 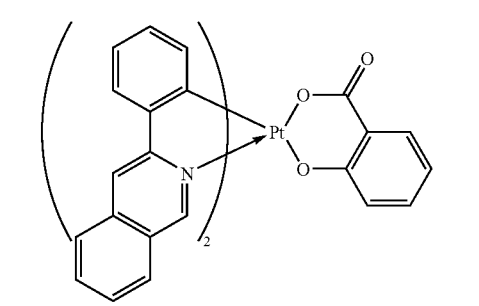
M057 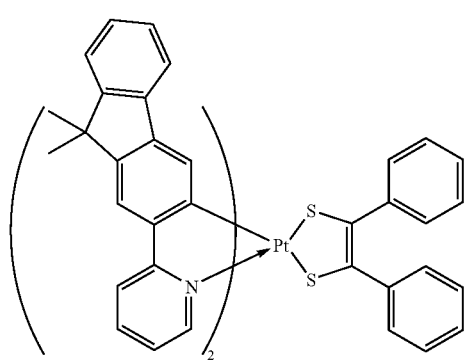
M058 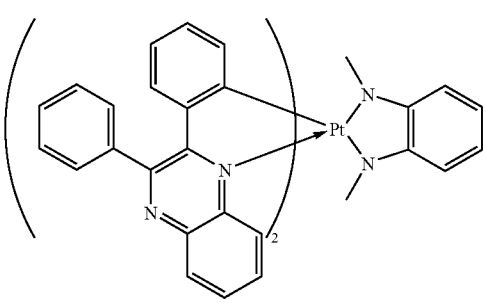
M059 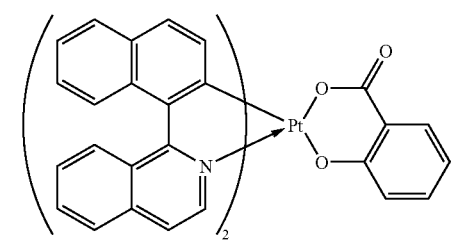
M060 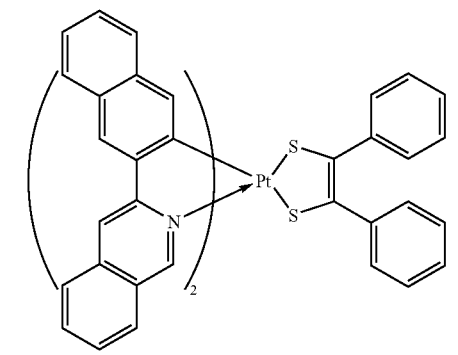
M061 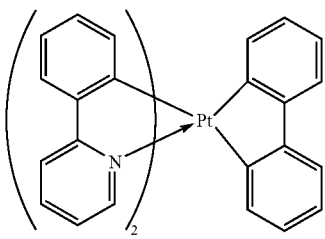
M062 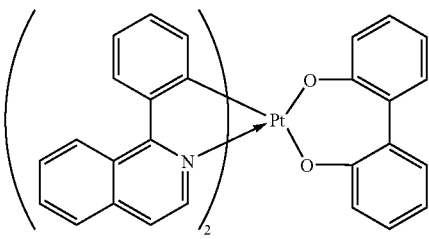
M063 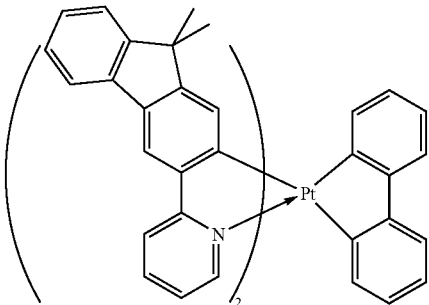
M064 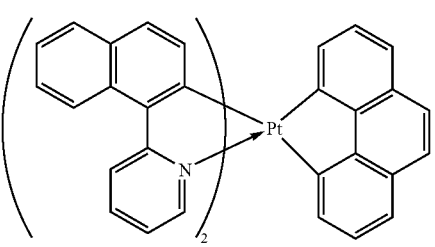
M065 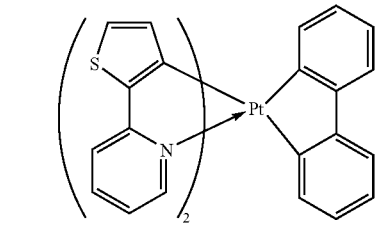
M066 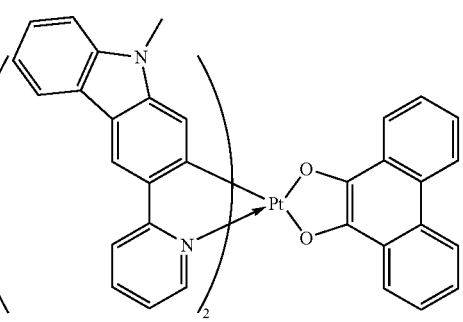

N001 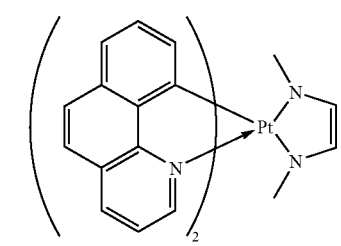
N002 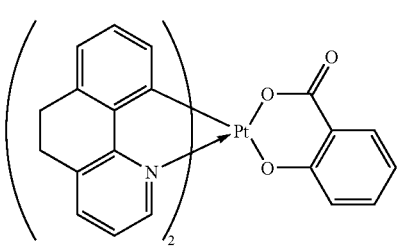
N003 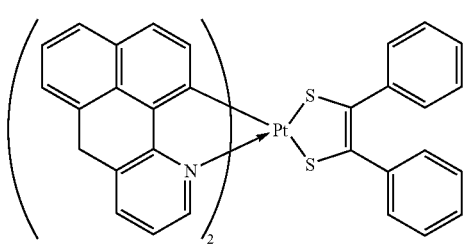
N004 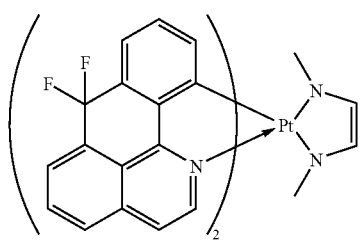
N005 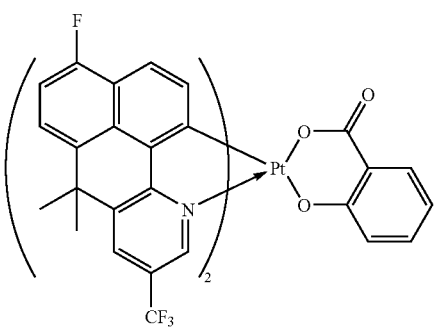
N006 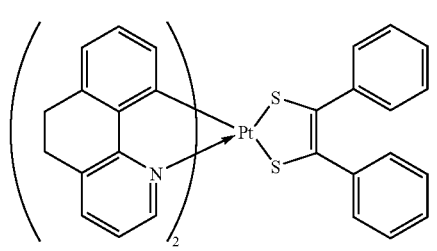
N007 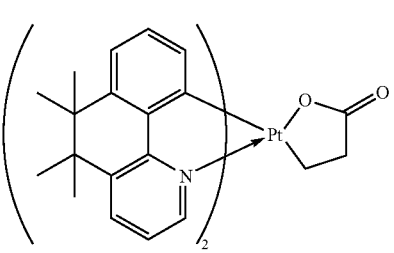
N008 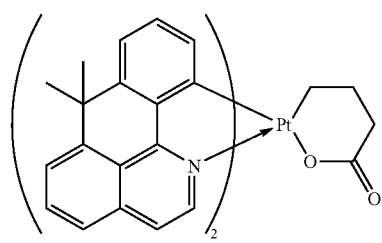
N009 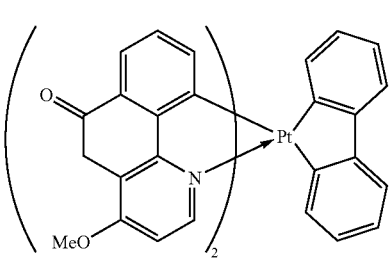
N010 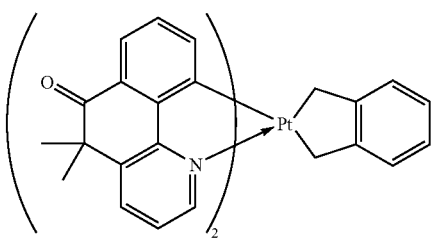
N011 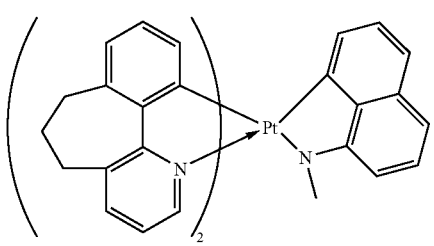
N012 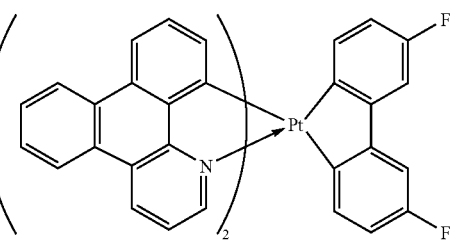

N013 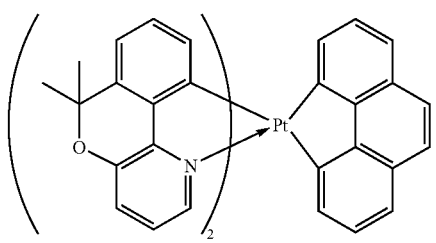
N014 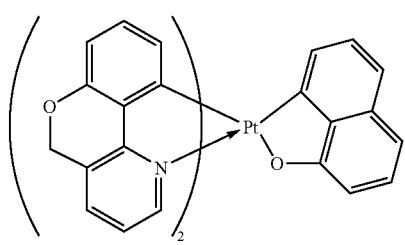
N015 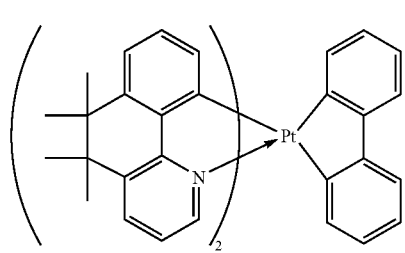
N016 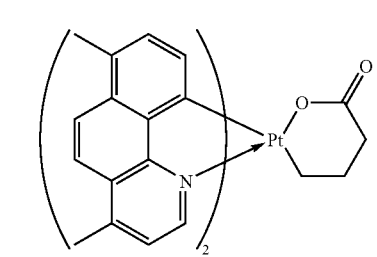
N017 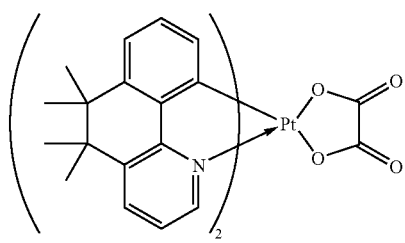
N018 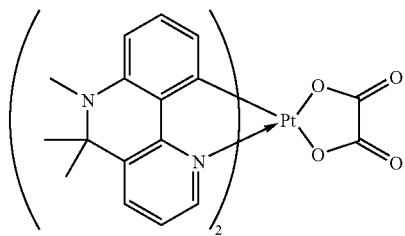
P001 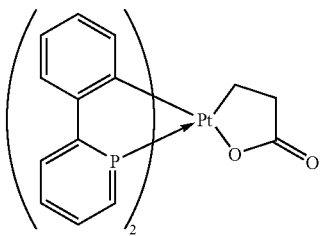
P002 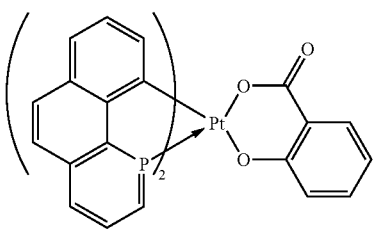
P003 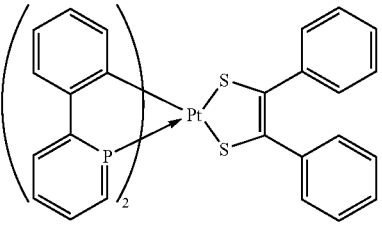
P004 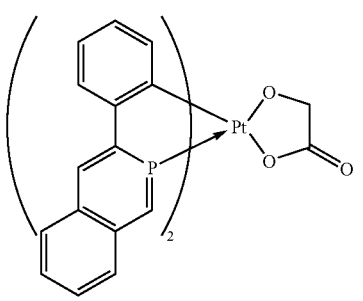
P005 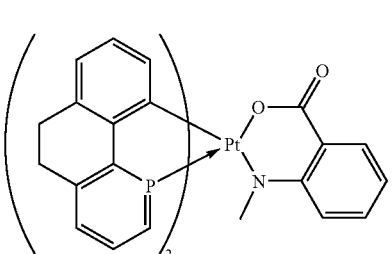
P006 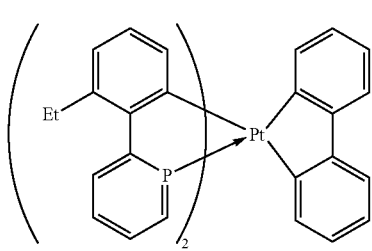

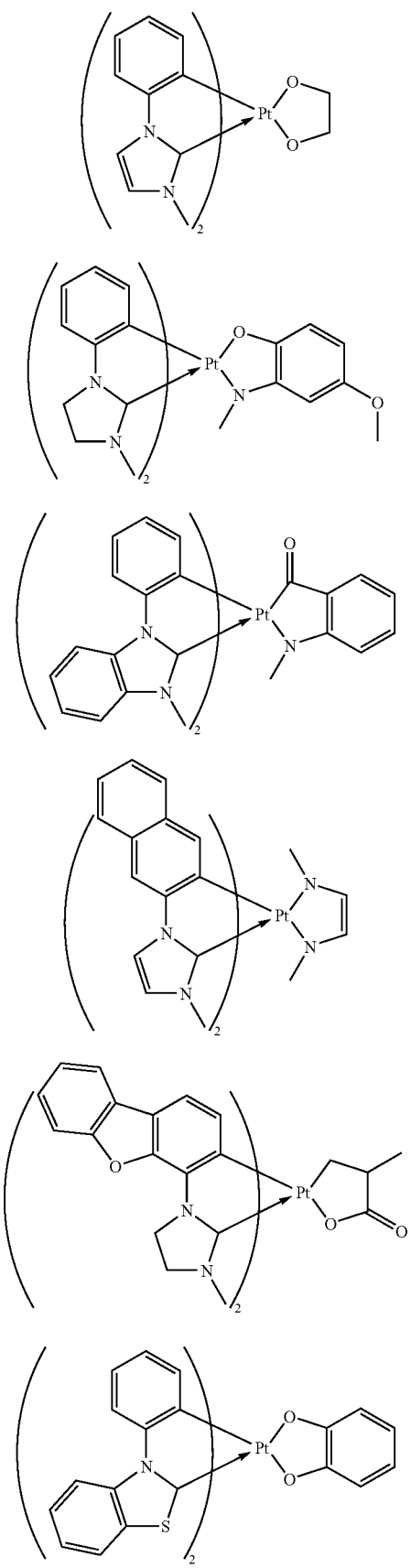

Q003 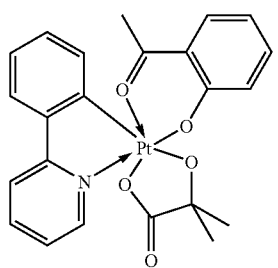
Q004 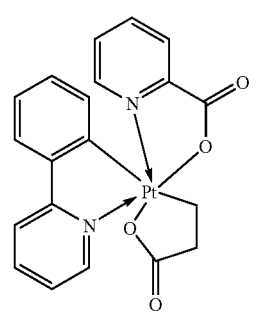
Q005 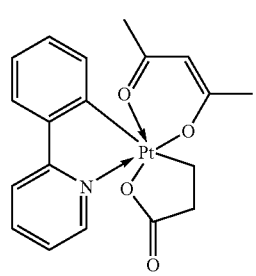
Q006 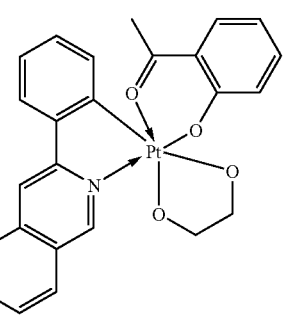
Q007 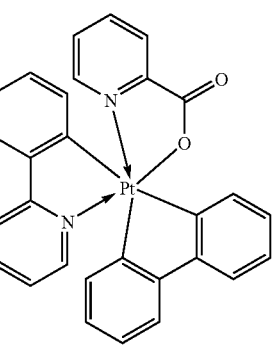
Q008 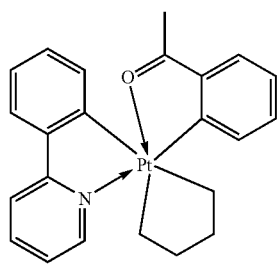
Q009 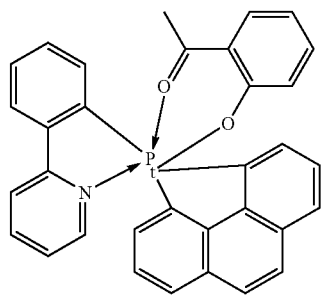
Q010 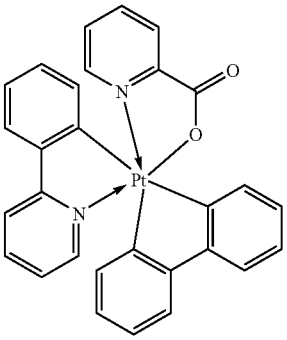
Q011 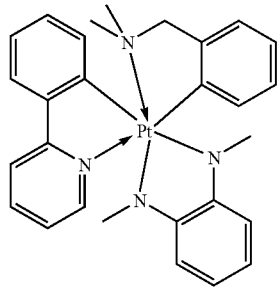
Q012 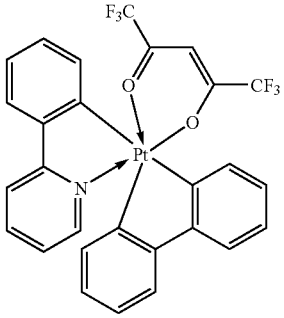

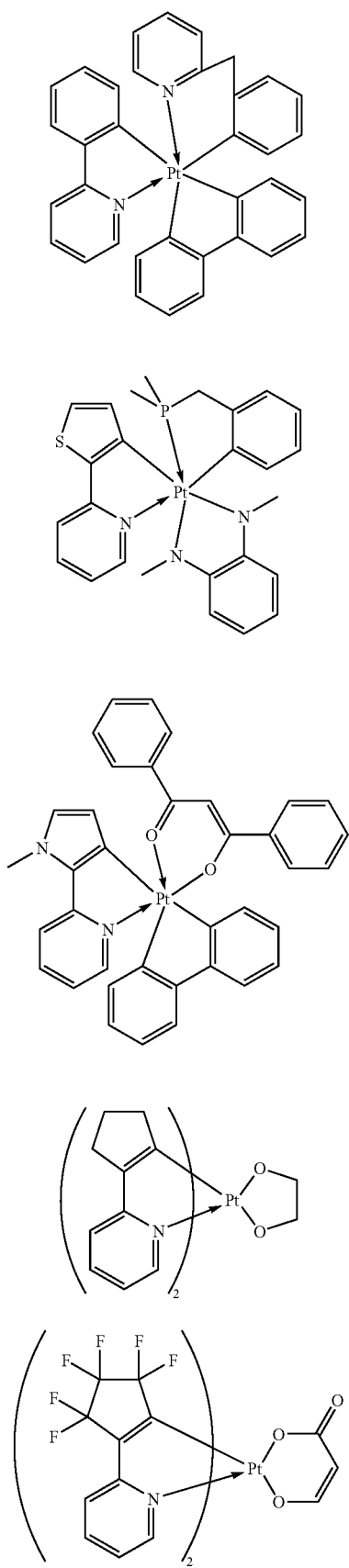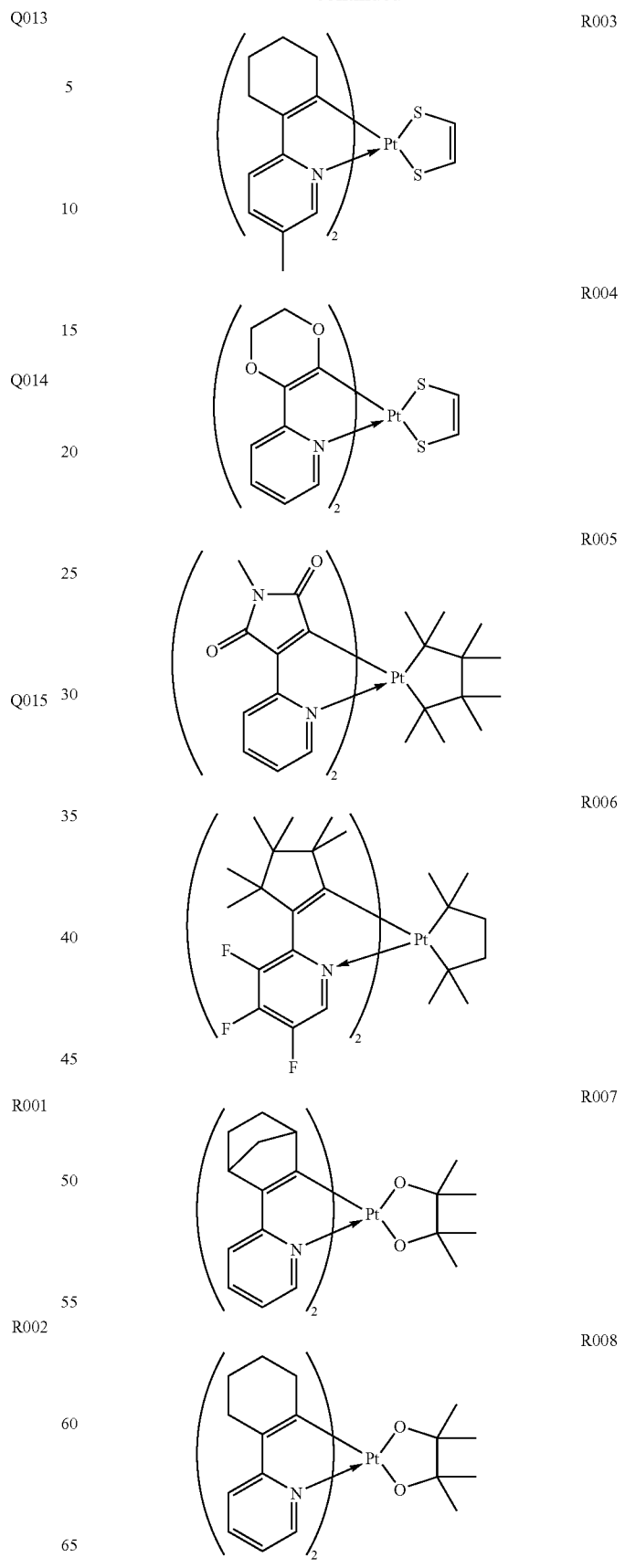

R009 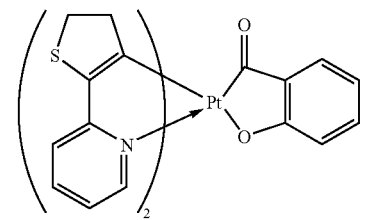
R010 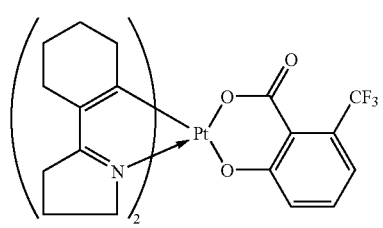
R011 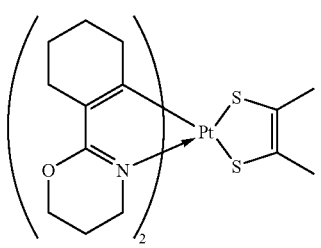
R012 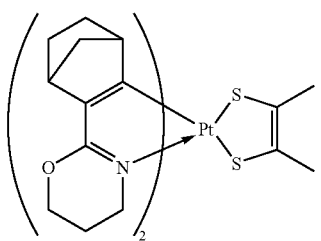
R013 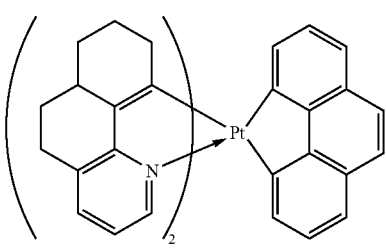
R014 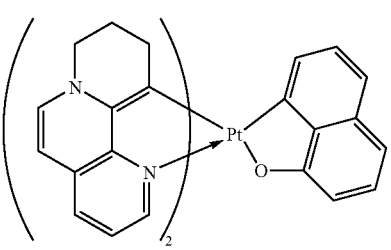
R015 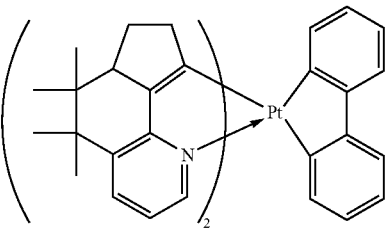
R016 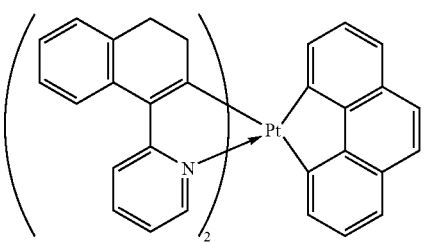
R017 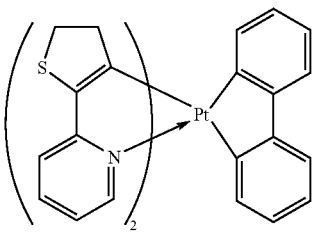
R018 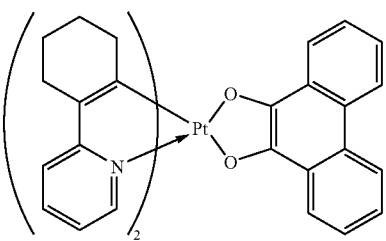
R019 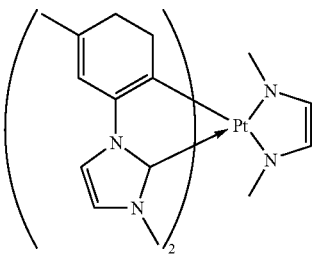
R020 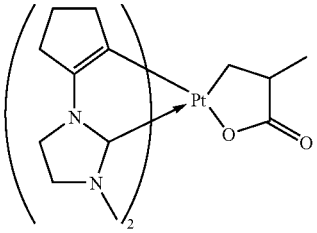

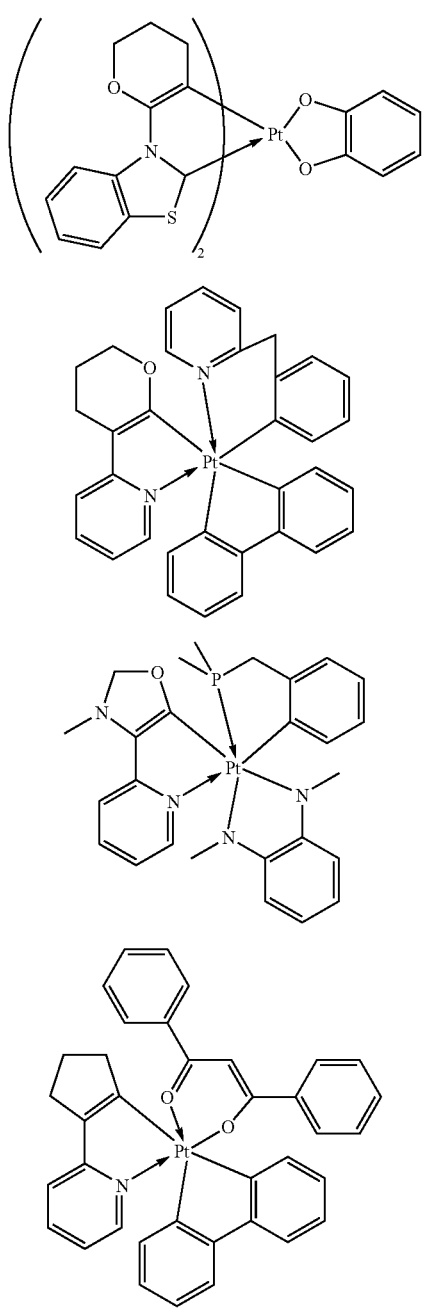

An embodiment of an organic light-emitting element in accordance with the present invention will be described below. The organic light-emitting element in accordance with the present invention comprises an anode, a cathode, and a layer of an organic compound sandwiched between the anode and the cathode.

The organic light-emitting element in accordance with the present invention will be described in more detail below with reference to the appended drawings.

The following reference numerals are used in the figures: 1—a substrate, 2—an anode, 3—a light-emitting layer, 4—a cathode, 5—a hole transport layer, 6—an electron transport layer, 7—a hole injection layer, 8—a hole/exciton blocking layer, and 10, 20, 30, 40, 50, 60—respective organic light-emitting elements.

FIG. 1 is a cross-sectional view illustrating a first embodiment of the organic light-emitting element in accordance with the present invention. In the organic light-emitting element 10 in FIG. 1, the anode 2, light-emitting layer 3, and cathode 4 are provided in the order of description on the substrate 1. The organic light-emitting element 10 shown in FIG. 1 may be useful, for example, when the light-emitting layer 3 comprises an organic compound combining hole transport ability, electron transport ability, and light emission ability. Further, the organic light-emitting element 10 may also be useful when the light-emitting layer 3 is obtained by mixing organic compounds each having at least one characteristic selected from among the hole transport ability, electron transport ability, and light emission ability.

Figure 2:
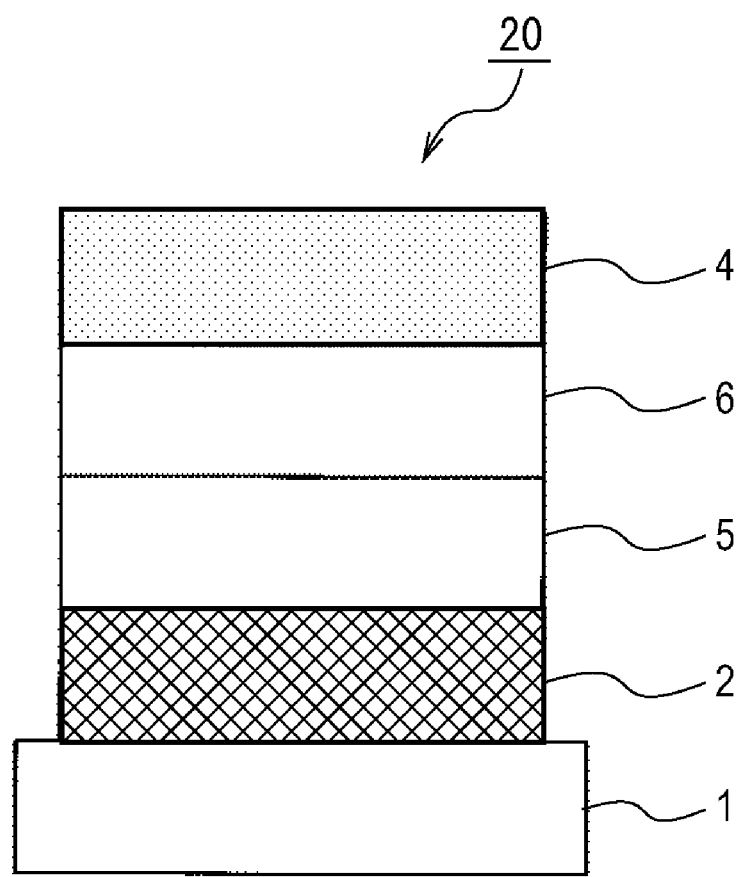
FIG. 2 is a cross-sectional view illustrating a second embodiment of the organic light-emitting element in accordance with the present invention.

FIG. 2 is a cross-sectional view illustrating a second embodiment of the organic light-emitting element in accordance with the present invention. In the organic light-emitting element 20 shown in FIG. 2, the anode 2, hole transport layer 5, electron transport layer 6, and cathode 4 are provided in the order of description on the substrate 1. This organic light-emitting element 20 may be useful, for example, when a light-emitting organic compound having any of hole transport ability and electron transport ability is used in combination with an organic compound having only the electron transport ability or only the hole transport ability. Further, in the organic light-emitting element 20, the hole transport layer 5 or electron transport layer 6 may also serve as a light-emitting layer 3.

Figure 3:
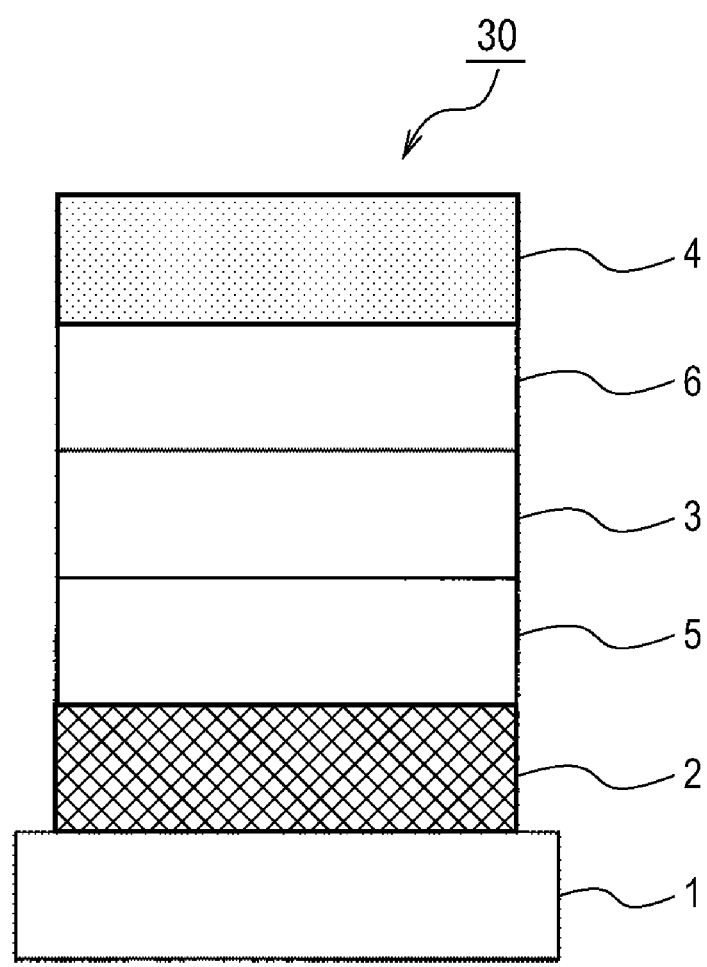
FIG. 3 is a cross-sectional view illustrating a third embodiment of the organic light-emitting element in accordance with the present invention.

FIG. 3 is a cross-sectional view illustrating a third embodiment of the organic light-emitting element in accordance with the present invention. The organic light-emitting element 30 shown in FIG. 3 has a configuration similar to the organic light-emitting element 20 shown in FIG. 2, however with the light-emitting layer 3 provided between the hole transport layer 5 and the electron transport layer 6. In this organic light-emitting element 30, the carrier transport function and the light emission function are separated, and compounds having respective characteristics from among the hole transport ability, electron transport ability, and light emission ability can be used in appropriate combinations. As a result, the degree of freedom in selecting suitable materials may be greatly increased and various compounds with different emission wavelengths can be used. Therefore, a variety of emission hues can be obtained. Furthermore, it may also be possible to confine effectively the carriers or excitons within the central light-emitting layer 3, thereby increasing the emission efficiency of the organic light-emitting element 30.

Figure 4:
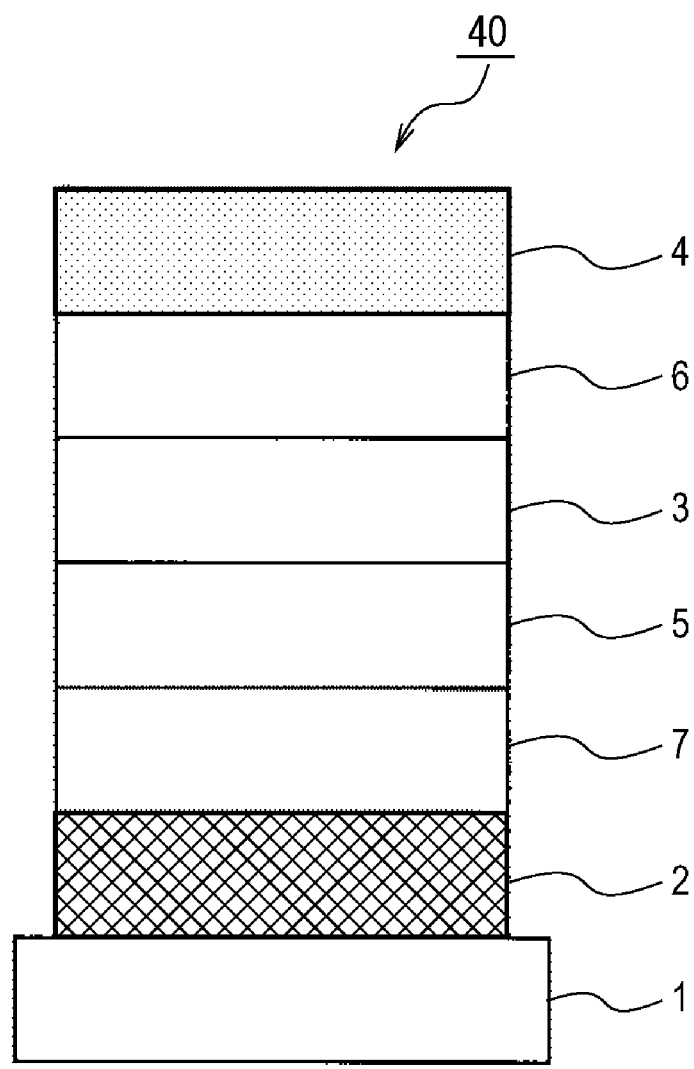
FIG. 4 is a cross-sectional view illustrating a fourth embodiment of the organic light-emitting element in accordance with the present invention.

FIG. 4 is a cross-sectional view illustrating a fourth embodiment of the organic light-emitting element in accordance with the present invention. The organic light-emitting element 40 shown in FIG. 4 has a configuration similar to the organic light-emitting element 30 shown in FIG. 3, however with a hole injection layer 7 being provided between the anode 2 and the hole transport layer 5. Because the hole injection layer 7 is provided in the organic light-emitting element 40, the adhesion of the anode 2 and hole transport layer 5 and the hole injection ability may be improved. Therefore, the voltage supplied may be effectively reduced.

Figure 5:
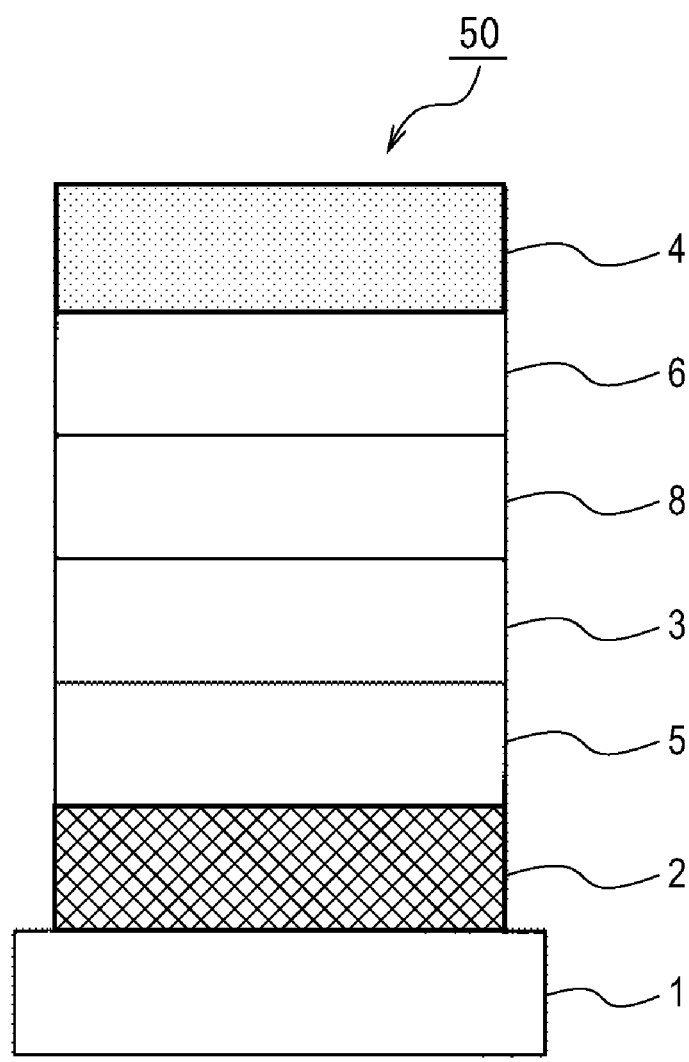
FIG. 5 is a cross-sectional view illustrating a fifth embodiment of the organic light-emitting element in accordance with the present invention.

FIG. 5 is a cross-sectional view illustrating a fifth embodiment of the organic light-emitting element in accordance with the present invention. The organic light-emitting element 50 shown in FIG. 5 has a configuration similar to the organic light-emitting element 30 shown in FIG. 3, however with a layer (hole/exciton blocking layer 8) that blocks the penetration of holes or excitons to the cathode side provided between the light-emitting layer 3 and the electron transport layer 6. By using a compound with a very high ionization potential as a constituent material for the hole/exciton blocking layer 8, it may be possible to increase the emission efficiency.

Figure 6:
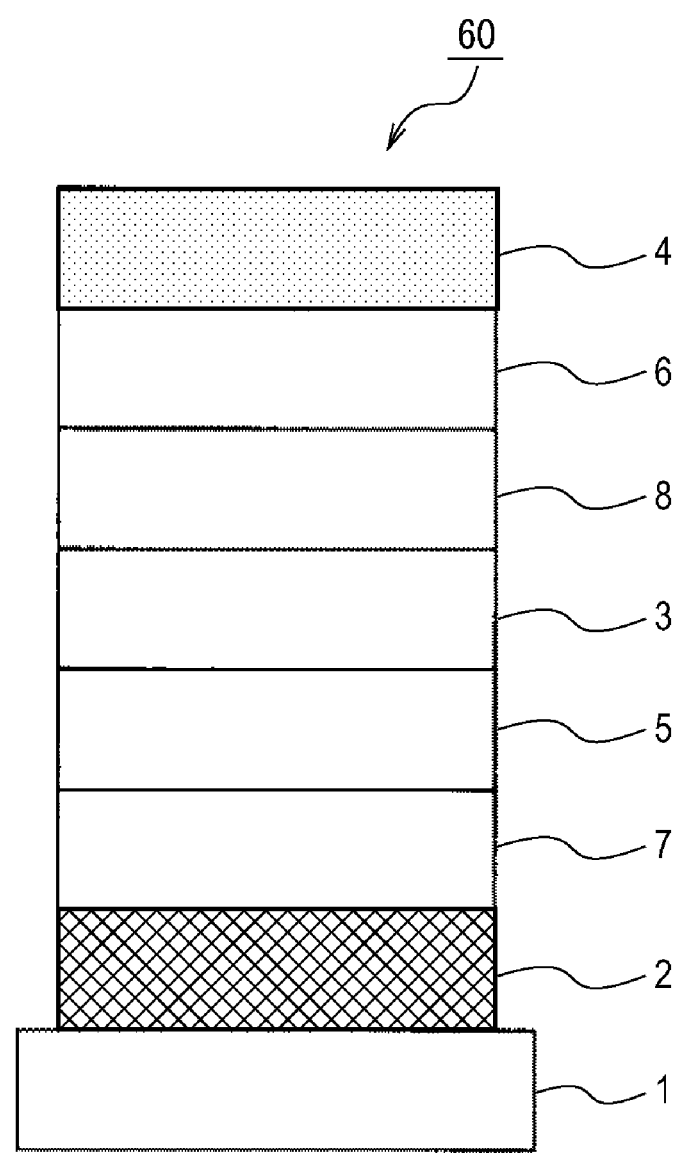
FIG. 6 is a cross-sectional view illustrating a sixth embodiment of the organic light-emitting element in accordance with the present invention.

FIG. 6 is a cross-sectional view illustrating a sixth embodiment of the organic light-emitting element in accordance with the present invention. The organic light-emitting element 60 shown in FIG. 6 has a configuration similar to the organic light-emitting element 40 shown in FIG. 4, however with the hole/exciton blocking layer 8 being provided between the light-emitting layer 3 and the electron transport layer 6. By using a compound with a very high ionization potential as a constituent material for the hole/exciton blocking layer 8, it may be possible to increase the emission efficiency.

FIG. 1 to FIG. 6 show examples of very basic element configurations, and the configuration of the organic light-emitting element using the platinum complex in accordance with the present invention is not intended to be limited to these particular configurations. For example, an insulating layer, an adhesive layer, or an interference layer may be provided on the interfaces of electrodes and layers composed of organic compounds. Furthermore, the hole transport layer 5 may be composed of a plurality of layers with different ionization potentials. In addition, the electron transport layer 6 may be a multilayer laminated body composed of an organic material layer and a layer obtained by vapor co-deposition of an organic material and alkali metal ions, alkali metal salts, and the like.

The platinum complex in accordance with the present invention can be used in any of the forms shown in FIGS. 1 to 6. In the organic light-emitting element in accordance with the present invention, at least one kind of the platinum complex in accordance with the present invention is contained in the layer comprising an organic compound. Here, the layer comprising an organic compound may be at least one of the light-emitting layer 3, hole transport layer 5, electron transport layer 6, hole injection layer 7, and hole/exciton blocking layer 8 shown in FIG. 1 to FIG. 6. In one version, the complex may be included in the light-emitting layer 3.

In one embodiment, the light-emitting layer 3 may be configured only with the platinum complex in accordance with the present invention. In another version, the light-emitting layer 3 may be configured with both a guest and a host.

In one version, when the platinum complex in accordance with the present invention is used as a host of the light-emitting layer 3, one or more of the compounds represented by the following formulas can be used as the corresponding guest.

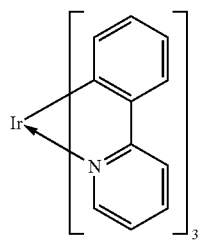

DD-1

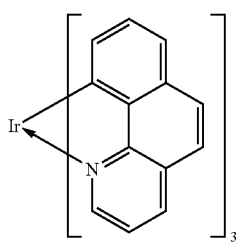

DD-2

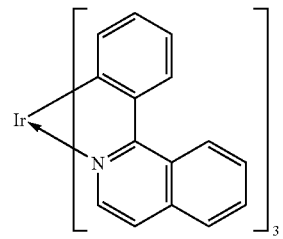

DD-3

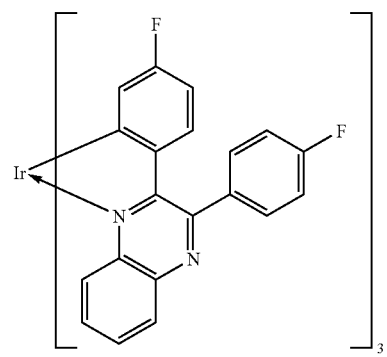

DD-4

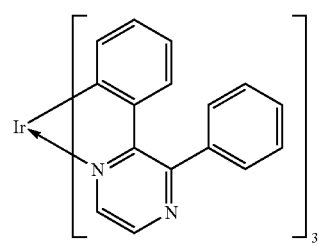

DD-5

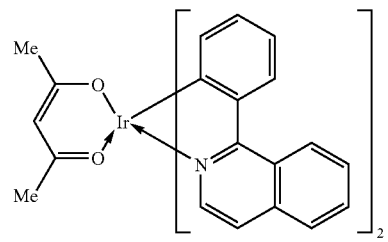

DD-6

When the platinum complex in accordance with the present invention is used as a host of the light-emitting layer 3, the content ratio of the platinum complex may be equal to or higher than 50 wt. % and equal to or lower than 99.9 wt. % based on the entire constituent material of the light-emitting layer 3.

In yet another version, the platinum complex in accordance with the present invention may be used as a light-emitting material (guest) of the light-emitting layer 3. In this version, the compounds represented by the following formulas can be used as the corresponding host.

DH-1
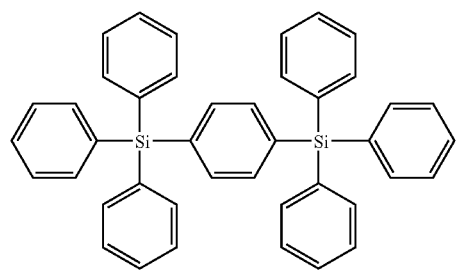
DH-2
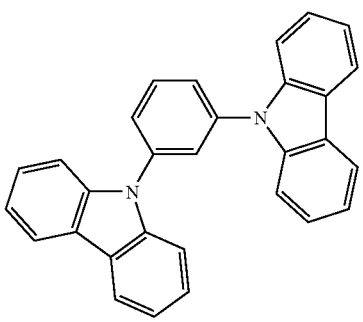
DH-3
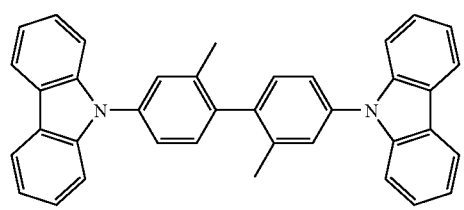
DH-4
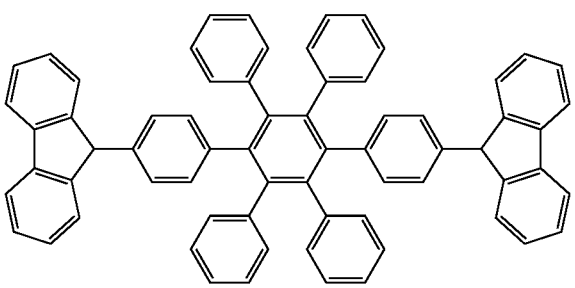
DH-5
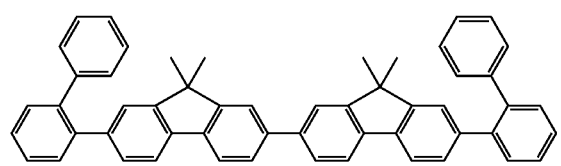
DH-6
DH-7
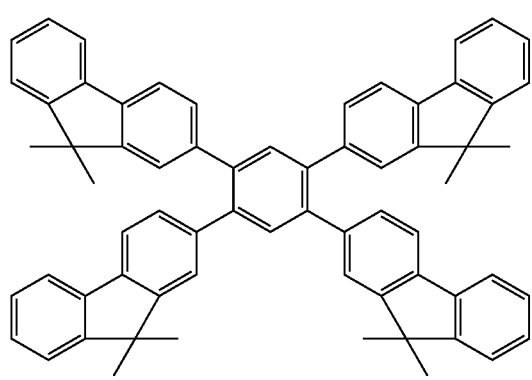
DH-8
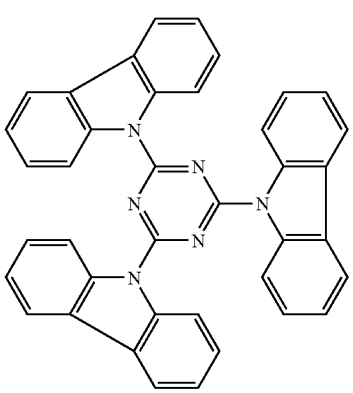
DH-9
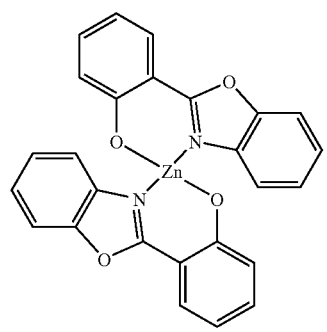
DH-10
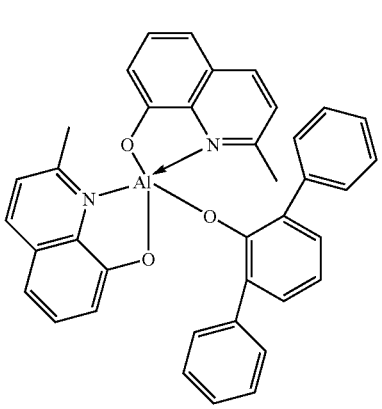

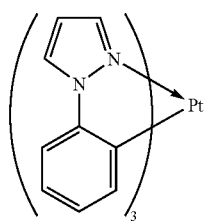

DH-11

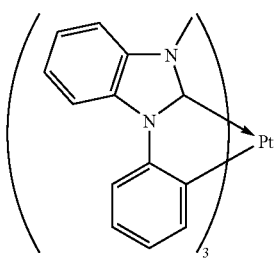

DH-12

When the platinum complex in accordance with the present invention is used as a guest of the light-emitting layer 3, the content ratio of the platinum complex may be equal to or higher than 0.1 wt. % and equal to or lower than 50 wt. %, such as equal to or higher than 0.1 wt. % and equal to or lower than 20 wt. %, based on the entire constituent material of the light-emitting layer 3.

The layer comprising an organic compound including the platinum complex in accordance with the present invention can be produced by, for example, at least one of a vacuum vapor deposition method, a casting method, a coating method, a spin coating method, an ink jet method, or the like. Further, other organic compound layers that do not contain the platinum complex in accordance with the present invention can be prepared by similar methods.

EXAMPLES

The present invention will be specifically described below with reference to the Examples, but the present invention is not limited thereto.

Example 1

Synthesis of Example Compound M025

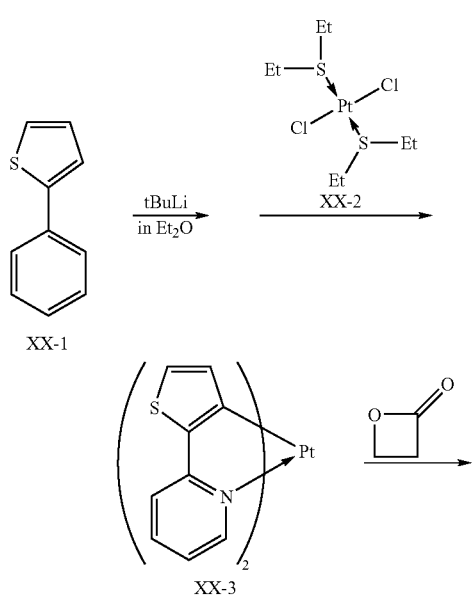

M025

(1) Synthesis of a compound XX-3 was carried out according to Inorg. Chem., 26, 2814-2818 (1987). First, a compound XX-1 (2.41 g, 15 mmol) was dissolved in ether (30 mL), and the reaction solution was then cooled to −78° C. Then, 1.7M tertiary butyllithium (10.0 mL, 17 mmol) was gradually dropwise added thereto. The reaction solution was then stirred for 30 min at −78° C. A compound XX-2 (1.4 g, 3.1 mmol) was then dissolved in 48 mL of diethylether, and the ether solution cooled to −78° C. was gradually dropwise added using a cannula. The reaction solution was then stirred for 30 min at −78° C., followed by gradual decrease of temperature to 0° C. Then, stirring was performed for 3 h at 0° C., and water was then added to stop the reaction. An organic layer and a water layer were then separated by a fractionation operation. The organic layer was washed with a saturated saline solution, and the water layer was fractionation extracted with dichloromethane. The organic layers were then combined, dried with magnesium sulfate and subjected to low-pressure distillation to remove the solvent. The residue thus obtained was subjected to separation and purification by silica gel column chromatography (developing solvent: dichloromethane/hexane=3/2) to obtain the compound XX-3.

(2) The compound XX-3 (150 mg, 0.291 mmol) and anhydrous THF (5 mL) were charged into a pressure vessel with a capacity of 20 mL. Then, β-lactone (1.8 mL, 29.1 mmol) was further added, and the reaction solution was then heated to 80° C. and stirred for 24 h. The solvent was distilled off under reduced pressure, and the residue thus obtained was subjected to separation and purification by silica gel column chromatography (developing solvent: chloroform/methanol=10/1) to obtain 141 mg (0.24 mmol) of Example Compound M025 in the form of yellow crystals (yield 82%).

A molecular weight of 588.03 g/mol was confirmed with ESI-TOFMASS.

NMR measurements were performed with respect to the compound obtained. The measurement results are presented below.

$^1$H-NMR (CDCl$_3$, 300 MHz) σ (ppm): 8.94 (s, 1H), 7.97 (m, 1H), 7.69-7.47 (m, 5H), 7.40 (m, 1H), 7.35 (m, 1H), 7.21 (m, 1H), 6.89 (m, 1H), 6.24 (m, 1H), 2.94 (m, 1H), 2.29 (m, 2H), 1.64 (m, 1H). Other example compounds in accordance with the present invention may be prepared according to the synthetic method described in Example 1 or methods similar thereto.

Example 2

An organic light-emitting element according to the embodiment shown in FIG. 2, in which the layer having the organic compound corresponds to a two-layer configuration, was manufactured.

A transparent electrode (anode 2) was formed by patterning ITO on a glass substrate (substrate 1). The thickness of the transparent electrode was 100 nm. The glass substrate in which the ITO was thus patterned will be referred to hereinbelow as an ITO-attached substrate.

PEDOT: PSS (H. C. Stark Co., Baytron P AI 4083), which is a mixture of the PEDOT and PSS materials shown below, was dropped on the ITO-attached substrate and spin coated at 4000 rpm to form the hole transport layer 5. The thickness of the hole transport layer was 30 nm.

PEDOT:

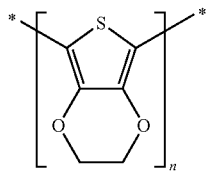

PSS:

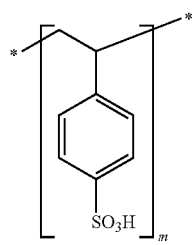

A coating liquid was prepared by mixing the below-described reagent and solvent.
Chloroform: 99 wt. %.
PVK (Aldrich Co.): 0.9 wt. %.

PVK:

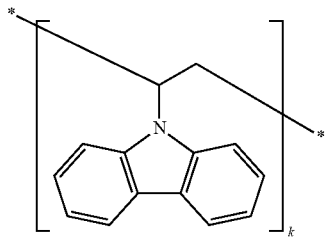

Example Compound M025: 0.1 wt. %.

The coating liquid was dropped on the hole transport layer 5 and spin coated at 2000 rpm to form the electron transport layer 6. The thickness of the electron transport layer 6 was 30 nm.

Then, drying was performed at 80° C. in a nitrogen atmosphere, $CsCO_3$ was then vapor deposited, and a first metal electrode was formed. The thickness of the first metal electrode was 2 nm. Then, Al was vapor deposited and a second metal electrode was formed. The thickness of the second metal electrode was 100 nm. The first metal electrode and second metal electrode functioned as the cathode 4.

An organic light-emitting element was thus obtained.

When a voltage of 10 V was applied, the obtained organic light emitting element was confirmed to emit green light. The element of the present embodiment was confirmed to maintain good light emission under nitrogen atmosphere.

The platinum complex according to the examples may be capable of realizing an organic light-emitting element of high efficiency and excellent stability.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions. This application claims the benefit of Japanese Patent Application No. 2007-286104, filed Nov. 2, 2007, which is hereby incorporated by reference herein in its entirety.

What is claimed is:

1. A platinum complex represented by General Formula (1) below

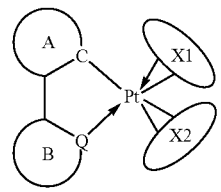

(1)

wherein in Formula (1)
Pt represents a tetravalent platinum atom;
the ring structure A represents a cyclic substituent having a carbon atom that forms a covalent bond with Pt, and wherein the ring structure A may also optionally contain a halogen atom, a nitro group, a substituted or unsubstituted aryl group, a substituted or unsubstituted heteroaryl group, a disubstituted amino group, or a linear or branched alkyl group having 1 to 20 carbon atoms;
the ring structure B represents a cyclic substituent having Q that forms a coordination bond with Pt, wherein Q is a carbon atom, a nitrogen atom, or a phosphorous atom, and wherein the ring structure B may also optionally contain a halogen atom, a nitro group, a substituted or unsubstituted aryl group, a substituted or unsubstituted heteroaryl group, a disubstituted amino group, or a linear or branched alkyl group having 1 to 20 carbon atoms;
wherein, optionally, a new ring structure may be formed by binding a substituent of the ring structure A to a substituent of the ring structure B;
X1 represents a monovalent-bidentate ligand; and
X2 represents a divalent-bidentate ligand having a carbon atom and an oxygen atom that form covalent bonds with the platinum atom.

2. The platinum complex according to claim 1, represented by General Formula (2) below

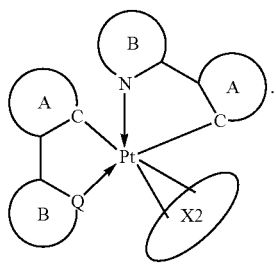

(2)

3. The platinum complex according to claim 1, wherein the Q is a nitrogen atom.

4. The platinum complex according to claim 1, wherein the ring structure A is an aromatic cyclic substituent.

5. An organic light-emitting element comprising:
   an anode and a cathode; and
   a layer comprising an organic compound that is sandwiched between the anode and the cathode, wherein
   at least one platinum complex according to claim 1 is contained in the layer comprising the organic compound.

6. The organic light-emitting element according to claim 5, wherein
   the layer comprising the organic compound is a light-emitting layer having the platinum complex contained therein.

7. The organic light-emitting element according to claim 6, wherein
   the light-emitting layer comprises a host and a guest.

\* \* \* \* \*